(12) United States Patent
Nemati et al.

(10) Patent No.: US 12,380,338 B2
(45) Date of Patent: Aug. 5, 2025

(54) CODES TO DETECT INSERTION AND DELETION ERRORS IN A DENSE STORAGE MEDIUM

(71) Applicant: Microsoft Technology Licensing, LLC, Redmond, WA (US)

(72) Inventors: Majid Anaraki Nemati, San Diego, CA (US); Anthony Dwayne Weathers, San Diego, CA (US); Pablo Alejandro Ziperovich, San Diego, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 1186 days.

(21) Appl. No.: 17/195,339

(22) Filed: Mar. 8, 2021

(65) Prior Publication Data

US 2022/0284304 A1 Sep. 8, 2022

(51) Int. Cl.

| | |
|---|---|
| *G16B 40/10* | (2019.01) |
| *C12Q 1/6869* | (2018.01) |
| *G06N 3/123* | (2023.01) |
| *G06N 3/126* | (2023.01) |
| *H03M 13/23* | (2006.01) |

(Continued)

(52) U.S. Cl.
CPC ........... *G06N 3/126* (2013.01); *C12Q 1/6869* (2013.01); *G06N 3/123* (2013.01); *G16B 40/10* (2019.02); *H03M 13/23* (2013.01); *H03M 13/256* (2013.01); *H03M 13/2939* (2013.01)

(58) Field of Classification Search
CPC .. G06N 3/123; H03M 13/23; H03M 13/2939; H03M 13/256
See application file for complete search history.

(56) References Cited

U.S. PATENT DOCUMENTS 11,403,031 B2 *  8/2022  Weathers ............ G06F 11/1068
11,495,324 B2 * 11/2022  Yekhanin ............ G06F 16/2365
12,181,971 B1 * 12/2024  Nemati ............... G06F 12/0875
(Continued)

OTHER PUBLICATIONS

Conde-Canencia, Laura, and Lara Dolecek. "Nanopore DNA sequencing channel modeling." 2018 IEEE International Workshop on Signal Processing Systems (SiPS). IEEE, 2018. (Year: 2018).*

(Continued)

*Primary Examiner* — Jesse P Frumkin
(74) *Attorney, Agent, or Firm* — Ray Quinney & Nebeker P.C.; Adam K. Richards

(57) ABSTRACT

This disclosure describes systems and methods for detecting multiple insertion and deletion errors in the presence of substitution errors in a signal (such as a sequenced DNA string). A convolutional code that includes two or more component convolutional codes is used for encoding. Each of the two or more component convolutional codes generates only a subset of all possible outputs of the convolutional code. The subsets of the two or more component convolutional codes are disjoint from each other. Only one of the two or more convolutional codes is active at any given time. The two or more convolutional codes together define a super code. The two or more convolutional codes are time interlaced within the super code, and the super code defines the convolutional code. A trellis that includes two or more component trellises designed based on the two or more component convolutional codes is used for decoding.

20 Claims, 12 Drawing Sheets

(51) Int. Cl.
H03M 13/25 (2006.01)
H03M 13/29 (2006.01)

(56) References Cited

U.S. PATENT DOCUMENTS

| | | | | |
|---|---|---|---|---|
| 2011/0172975 | A1* | 7/2011 | Silva Filho | H03M 13/152 |
| | | | | 703/2 |
| 2021/0098081 | A1* | 4/2021 | Yekhanin | G06F 16/2365 |
| 2022/0166446 | A1* | 5/2022 | Yekhanin | H03M 7/6041 |
| 2023/0070921 | A1* | 3/2023 | Sabary | G16B 50/30 |
| 2023/0187024 | A1* | 6/2023 | Conde-Canencia | |
| | | | | H03M 13/611 |
| | | | | 703/11 |
| 2023/0419331 | A1* | 12/2023 | Owen | G11C 13/0019 |

OTHER PUBLICATIONS

A. Lenz, I. Maarouf, L. Welter, A. Wachter-Zeh, E. Rosnes et al., "Concatenated codes for recovery from multiple reads of DNA sequences," arXiv preprint arXiv:2010.15461, 2020. (Year: 2020).*

Chandak, Shubham, et al. "Overcoming high nanopore basecaller error rates for DNA storage via basecaller-decoder integration and convolutional codes." ICASSP 2020-2020 IEEE International Conference on Acoustics, Speech and Signal Processing (ICASSP). IEEE, 2020. (Year: 2020).*

Blawat, et al., "Storing Movies in DNA", In Focus on Future Disruptive Technologies—Innovation in Motion Summer 2015, Jan. 1, 2015, pp. 38-43.

Calderbank, et al., "Minimal Tail-Biting Trellises: The Golay Code and More", In Journal of IEEE Transactions on Information Theory, vol. 45, Issue 5, Jul. 1999, pp. 1435-1455.

Chandak, et al., "Overcoming High Nanopore Basecaller Error Rates for DNA Storage via Basecaller-Decoder Integration and Convolutional Codes", In Proceedings of IEEE International Conference on Acoustics, Speech and Signal Processing, May 4, 2020, pp. 8822-8826.

Cheng, et al., "Rate-compatible Pruned Convolutional Codes and Viterbi Decoding with the Levenshtein Distance Metric applied to Channels with Insertion, Deletion, and Substitution Errors", In Proceeding of 7th IEEE Africon Conference in Africa, Sep. 15, 2004, pp. 137-143.

Lee, Pil Joong, "There are Many Good Periodically Time-varying Convolutional Codes", In Journal of IEEE Transactions on Information Theory, vol. 35, Issue 2, Mar. 1989, pp. 460-463.

Lenz, et al., "Concatenated Codes for Recovery From Multiple Reads of DNA Sequences", In repository of arXiv:2010.15461v1, Oct. 29, 2020, 5 Pages.

"International Search Report and Written Opinion Issued in PCT Application No. PCT/US22/017448", Mailed Date: May 17, 2022, 16 Pages.

Perez, Lance C., "Time Varying Convolutional Codes Revisited", In Proceedings 2001 IEEE Information Theory Workshop, Sep. 2, 2001, pp. 67-69.

Saouter, "Time Varying Convolutional Codes for Punctured Turbocodes", In 2011 Wireless Telecommunications Symposium, Apr. 13, 2011, 5 Pages.

Guruswami, et al., "Efficiently decodable insertion/deletion codes for high-noise and high-rate regimes", In Repository of arXiv:1605.04611v1, May 15, 2016, 5 Pages.

Levenshtein, V.I, "Binary Codes Capable of Correcting Deletions, Insertions, and Reversals", In Journal of Soviet Physics Doklady, vol. 10, No. 8, Feb. 10, 1966, pp. 707-710.

Schoeny, et al., "Codes Correcting a Burst of Deletions or Insertions", In Repository of arXiv:1602.06820v2, May 12, 2016, pp. 1-19.

Sloane, N. J. A., "On Single-Deletion-Correcting Codes", In Repository of arXiv:math/0207197v1, Jul. 22, 2002, pp. 1-23.

Tatwawadi, et al., "Tutorial on algebraic deletion correction codes", In Repository of arXiv:1906.07887v1, Jun. 19, 2019, pp. 1-9.

* cited by examiner

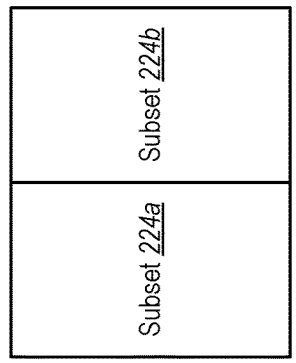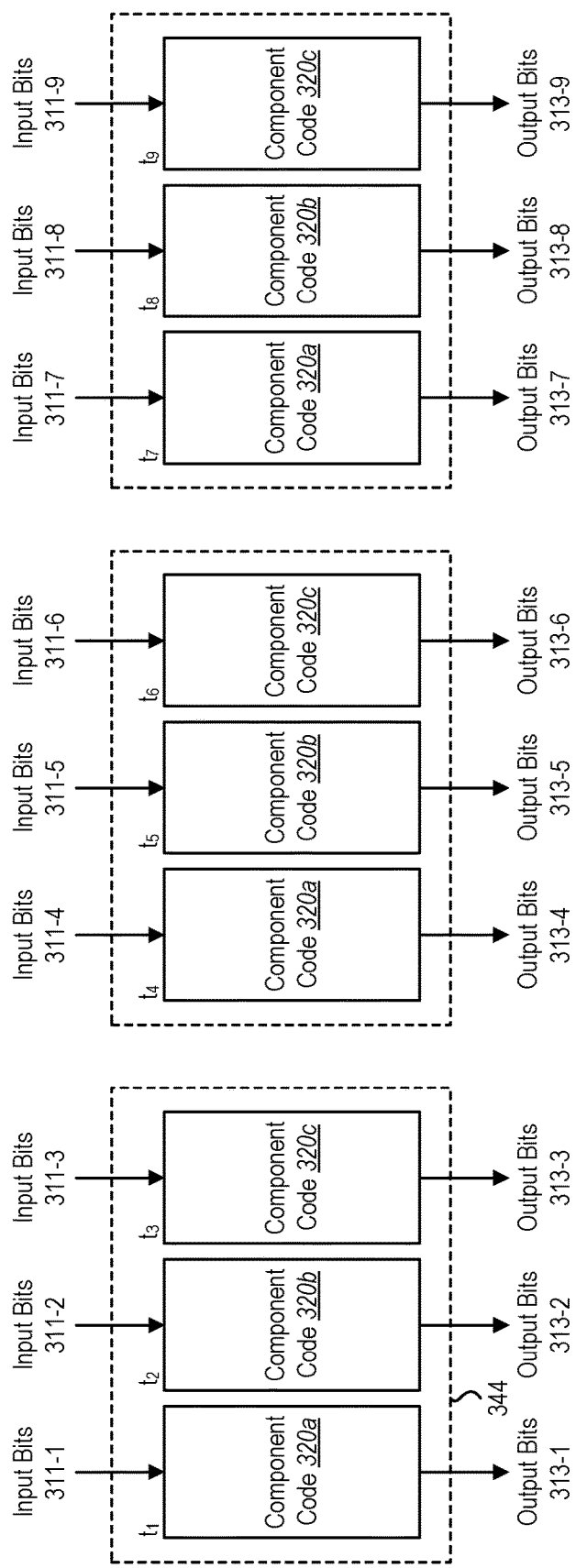

Set of Possible Outputs 322

1

CODES TO DETECT INSERTION AND DELETION ERRORS IN A DENSE STORAGE MEDIUM

CROSS-REFERENCE TO RELATED APPLICATIONS

N/A

BACKGROUND

DNA data storage involves encoding binary data into synthesized strands of DNA and then sequencing and decoding the synthesized strands of DNA. DNA storage is much denser and more durable than silicon-based electronic storage. But DNA storage presents unique challenges. In DNA storage, unlike traditional communication/storage channels, symbol insertion and deletion happen frequently in addition to symbol substitutions. For example, during the process of synthesizing a strand of synthetic DNA, symbols may be added or deleted.

One way to minimize the probability of insertion and deletion errors in sequencing synthetic DNA is to sequence the same strand of synthetic DNA multiple times. The sequenced strings are then compared to estimate a final string. Because sequenced strings contain insertion, deletion, and substitution errors, it is often necessary to combine a large number of copies to meet a required reliability threshold. One drawback of this method is that sequencing is an inherently time-consuming process. Indeed, one of the problems generally with DNA storage is that it suffers from a delay between the time the host requests the data and the time the data can be delivered to the host. Performing multiple sequencing operations exacerbates this delay.

SUMMARY

In accordance with one aspect of the present disclosure, a computer-readable medium is disclosed that includes instructions that are executable by one or more processors to cause a computing system to receive a first input at a first time. The instructions are also executable by the one or more processors to cause a computing system to determine, using a first set of convolutional code connections, a first output based on the first input and a first state. The first state is contained in convolutional code memories. The instructions are also executable by the one or more processors to cause a computing system to modify the convolutional code memories to generate a second state based on the first state, the first input, and the first set of convolutional code connections. The instructions are also executable by the one or more processors to cause a computing system to receive a second input at a second time after the first time. The instructions are also executable by the one or more processors to cause a computing system to determine, using a second set of convolutional code connections, a second output based on the second input and the second state. The first set of convolutional code connections is configured to produce outputs in a first subset of a set of possible outputs, the second set of convolutional code connections is configured to produce outputs in a second subset of the set of possible outputs, and the first subset is disjoint from the second subset. The instructions are also executable by the one or more processors to cause a computing system to modify the convolutional code memories to generate a third state based on the second state, the second input, and the second set of convolutional code connections.

The computer-readable medium may further include instructions that are executable by the one or more processors to cause the computing system to receive a third input at a third time after the second time. The instructions may also be executable by the one or more processors to determine, using the first set of convolutional code connections, a third output based on the third input and the third state. The instructions may also be executable by the one or more processors to modify the convolutional code memories to generate a fourth state based on the third state, the third input, and the first set of convolutional code connections.

The computer-readable medium may further include instructions that are executable by the one or more processors to cause the computing system to receive a third input at a third time after the second time. The computer-readable medium may further include instructions that are executable by the one or more processors to cause the computing system to determine, using a third set of convolutional code connections, a third output based on the third input and the third state. The third set of convolutional code connections may be configured to produce outputs in a third subset of the set of possible outputs and the third subset may be disjoint from the second subset and the first subset. The computer-readable medium may further include instructions that are executable by the one or more processors to cause the computing system to modify the convolutional code memories to generate a fourth state based on the third state, the third input, and the third set of convolutional code connections.

The computer-readable medium may further include instructions that are executable by the one or more processors to cause the computing system to map the first output to a first set of symbols and map the second output to a second set of symbols.

The first set of symbols and the second set of symbols may represent one or more DNA bases.

The first set of symbols may include a sequence of one or more DNA bases different from the second set of symbols.

The convolutional code memories may include two or more memories.

The first input may include two or more bits and the first output may include more bits than the first input.

In accordance with another aspect of the present disclosure, a computer-readable medium is disclosed that includes instructions that are executable by one or more processors to cause a computing system to receive, at a decoder, a first input at a first time, wherein the decoder has a first state at the first time. The instructions are also executable by the one or more processors to cause a computing system to calculate a first distance between the first input and a first set of valid inputs. The first set of valid inputs is defined by a first component trellis code. The instructions are also executable by the one or more processors to cause a computing system to determine a second state of the decoder based on the first state, the first input, and the first component trellis code. The instructions are also executable by the one or more processors to cause a computing system to receive, at the decoder, a second input at a second time after the first time. The instructions are also executable by the one or more processors to cause a computing system to calculate a second distance between the second input and a second set of valid inputs. The second set of valid inputs is defined by a second component trellis code. The second set of valid inputs is disjoint from the first set of valid inputs. The instructions are also executable by the one or more processors to cause a computing system to determine a third state of the decoder based on the second state, the second input, and the second component trellis code.

The first distance and the second distance may be one or more of L1 distances, L2 distances, or any other distance metric.

The computer-readable medium may further include instructions that are executable by the one or more processors to cause the computing system to determine, based on the first distance and the second distance, a location of an insertion or deletion error.

The computer-readable medium may further include instructions that are executable by the one or more processors to cause the computing system to receive a third input at a third time after the second time, calculate a third distance between the third input and the first set of valid inputs, and determine a fourth state of the decoder based on the third state, the third input, and the first component trellis code.

The computer-readable medium may further include instructions that are executable by the one or more processors to cause the computing system to receive a third input at a third time after the second time and calculate a third distance between the third input and a third set of valid inputs. The third set of valid inputs may be defined by a third component trellis code. The third set of valid inputs may be disjoint from the first set of valid inputs and the third set of valid inputs. The instructions may also be executable by the one or more processors to cause the computing system to determine a fourth state of the decoder based on the third state, the third input, and the third component trellis code.

The first input and the second input may be sequenced from DNA storage.

The first input and the second input may represent one or more DNA bases.

In accordance with another aspect of the present disclosure, a method is disclosed for detecting deletion and insertion errors. The method includes encoding a set of inputs using a convolutional encoder to produce a set of encoded outputs. The convolutional encoder includes a first component convolutional code and a second component convolutional code, the first component convolutional code produces outputs within a first subset of a set of possible outputs, the second component convolutional code produces outputs within a second subset of the set of possible outputs, and the first subset is disjoint from the second subset. The method also includes receiving, at a decoder, a set of encoded inputs. Each encoded input in the set of encoded inputs represents a sequence of one or more symbols. The decoder includes a first component trellis code and a second component trellis code. The first component trellis code defines a first set of valid inputs, the second component trellis code defines a second set of valid inputs, the first set of valid inputs is equivalent to the first subset of possible outputs, and the second set of valid inputs is equivalent to the second subset of possible outputs. The method also includes determining a distance between each encoded input in the set of encoded inputs and an applicable set of valid inputs to produce a set of distances. The applicable set of valid inputs switches between the first set of valid inputs and the second set of valid inputs. The method also includes producing a set of decoded outputs for the set of encoded inputs. The set of decoded outputs is determined based on the first component trellis code and the second component trellis code. The method also includes identifying, based on the set of distances, insertion and deletion errors in the set of encoded inputs. The method also includes modifying, based on identifying the insertion and deletion errors in the set of encoded inputs, the set of decoded outputs to produce a modified set of decoded outputs.

The method may further include providing the modified set of decoded outputs to an error correction code.

The method may further include mapping each output in the set of encoded outputs to a combination of one or more symbols.

The combination of one or more symbols may include DNA bases.

The set of encoded inputs may include substitution errors.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description that follows. Features and advantages of the disclosure may be realized and obtained by means of the systems and methods that are particularly pointed out in the appended claims. Features of the present disclosure will become more fully apparent from the following description and appended claims, or may be learned by the practice of the disclosed subject matter as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. Understanding that the drawings depict some example embodiments, the embodiments will be described and explained with additional specificity and detail through the use of the accompanying drawings in which:

FIG. 2B illustrates an example division of a set of possible outputs into two subsets in order to enable detection of multiple insertion and deletion errors in a signal.

FIG. 3A illustrates an example code consisting of three component codes that enable detection of multiple insertion and deletion errors in a signal.

DETAILED DESCRIPTION

Figure 1:
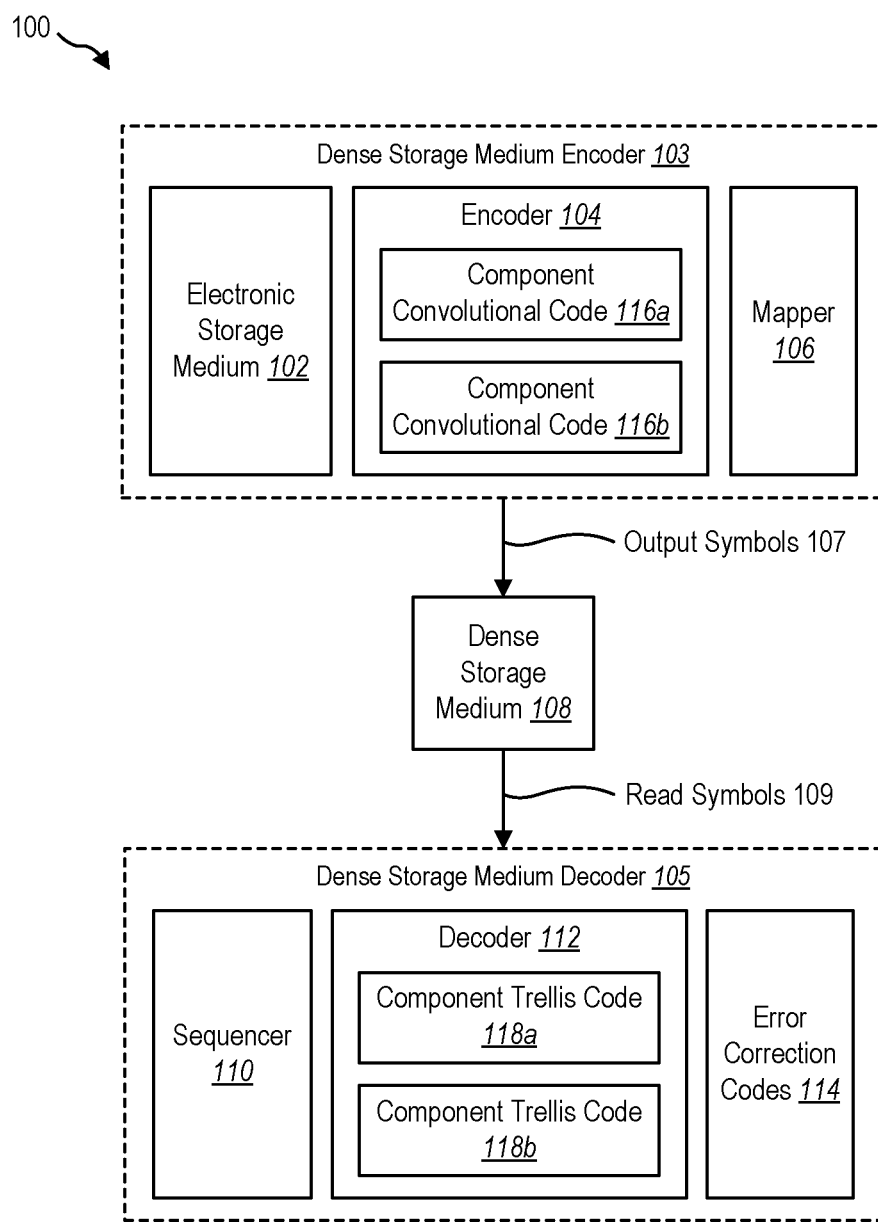
FIG. 1 illustrates an example system for encoding and decoding data such that the system can detect multiple insertion and deletion errors in the presence of substitution errors.

This disclosure concerns systems and methods for detecting multiple deletion and insertion errors in signals. The signals may represent symbols read from a storage medium, such as a DNA storage. The systems and methods use codes that include two or more component codes (such as two or more component convolutional codes or two or more component trellis codes). The two or more component codes are time interlaced and are designed to produce disjoint outputs (or define disjoint sets of valid inputs). The disclosed systems and methods allow for detection of multiple deletions and insertions even when substitution errors are present and even when deletions and insertions occur in clusters. The disclosed systems and methods can be applied to detecting insertion and deletion errors in data retrieved from a DNA storage.

DNA data storage involves encoding and decoding binary data to and from synthesized strands of DNA. DNA storage is much denser and more durable than silicon-based electronic storage. Reading information from DNA storage involves sequencing chains of DNA bases (A, T, C, and G) stored in the synthetic DNA and decoding these chains into a form a computer can understand.

DNA storage presents unique challenges not necessarily present in traditional communication and storage channels. In traditional storage channels, symbol substitution errors may occur. For example, a bit may be flipped from 0 to 1. In DNA storage, unlike traditional communication/storage channels, symbol insertion and deletion (i.e., insertion or deletion of DNA bases) happen frequently in addition to symbol substitutions. For example, during the process of synthesizing a strand of synthetic DNA, DNA bases may be added to or deleted from the sequenced string. As another example, during the process of writing to a DNA storage, DNA bases may be added to or deleted from the written strand of synthetic DNA.

Insertions and deletions create problems for classical error correction codes. Traditional error correction codes may be efficient only in correcting substitution errors (i.e., errors in which one symbol in a string of symbols is replaced by a second symbol). Error correction codes in classic encoding and decoding are based on symbol location. Insertion and deletion errors, by changing the location of code symbols, cause all the code syndrome equations to become invalid. Therefore, such codes completely break in the presence of deletion or insertion errors.

One way to overcome insertion and deletion errors in sequencing synthetic DNA is to sequence the same strand of synthetic DNA multiple times and compare the sequenced strings to probabilistically estimate a final string. Because sequenced strings contain insertion, deletion, and substitution errors, it is often necessary to combine a large number of copies of the same DNA string to meet a required reliability threshold. One drawback of this method is that sequencing DNA is an inherently time-consuming process. Indeed, one of the problems generally with DNA storage is that it suffers from a delay between the time the host requests data and the time the data can be delivered to the host. Performing multiple sequencing operations only exacerbates this delay.

This disclosure describes systems and methods for detecting insertion and deletion errors in a dense storage medium, such as sequenced DNA strings. The systems and methods can detect multiple insertion and deletion errors in the presence of substitution errors. The systems and methods can modify decoded data based on the detected insertion and deletion errors such that traditional error correction codes can correct substitution errors. The systems and methods reduce the number of independent strings that need to be sequenced in order to meet a defined reliability threshold. Although the systems and methods may be described in connection with DNA storage, they can be applied to detecting insertion and deletion errors in connection with any signals or storage types.

The described systems and methods use a convolutional code that includes two or more component convolutional codes. A convolutional code is a type of error-correcting code that generates parity symbols via the sliding application of a Boolean polynomial function to a data stream. Signals encoded using a convolutional code can be decoded using trellis decoding. Each of the two or more component convolutional codes generates only a subset of all possible outputs of the convolutional code. The subsets of the two or more component convolutional codes are disjoint from each other. Only one of the two or more convolutional codes is active at any given time. The two or more convolutional codes together define a super code. The two or more convolutional codes are time interlaced within the super code, and the super code repeats and defines the convolutional code. The convolutional code changes to a new convolutional code within the two or more convolutional codes with each received input.

The described systems and methods include an encoder and a decoder designed based on the two or more component convolutional codes. The encoder may encode a signal consisting of a string of bits to enable identification of insertion and deletion errors. The decoder may decode signals encoded by the encoder and identify insertion and deletion errors in the encoded signals. The decoder may be a Viterbi decoder. The encoded signals may have passed through a storage channel, such as a DNA storage channel. Insertion and deletion errors may be introduced in the encoded signals in the process of writing to or reading from the storage channel.

The encoder includes two or more sets of connections based on the two or more component convolutional codes. Each of the two or more component convolutional codes has a corresponding set of connections. The two or more sets of connections share a set of memories. Each of the two or more sets of connections defines a feedback network among the memories. The set of memories define a state of the encoder.

The encoder applies only one of the two or more sets of connections at a time and switches among the two or more sets of connections. The encoder may switch from one set of connections to another set of connections with each received input. The two or more sets of connections may be time interlaced, and the encoder may apply each of the two or more sets of connections before reapplying each of the two or more sets of connections.

The encoder is designed to produce a set of possible outputs. Each of the two or more sets of connections is designed to produce outputs within a subset of the set of possible outputs. Each subset is disjoint from all other subsets. In other words, the set of possible outputs is divided into a number of disjoint subsets equal to a number of sets of connections, and each of the sets of connections in the two or more sets of connections is designed to produce only outputs within a particular subset. The encoder determines an output based on an input, the state of the encoder, and the applicable set of connections among the two or more sets of connections.

The decoder is designed to decode messages encoded by the encoder. The decoder may use a trellis to decode the messages. The decoder may receive encoded inputs and produce decoded outputs. The trellis includes two or more component trellises based on the two or more component convolutional codes. The two or more component trellises define a super trellis. The two or more component trellises are time interlaced within the super trellis, and the super trellis defines the decoder.

The two or more component trellises share a set of memories that define a state of the decoder. For each encoded input received by the decoder, the decoder determines a most probable next state based on the received input, the current state of the decoder, and the applicable component trellis. For each encoded input received by the decoder, the decoder determines a most probable decoded output based on the received input, the current state of the decoder, and the applicable component trellis.

Each of the two or more component trellises defines branches and symbols associated with each branch. Only one of the two or more component trellises defines the branches and the symbols associated with each branch at a time. The decoder switches among the two or more component trellises to obtain the branches and the symbols associated with the branches. In this way, each of the two or more component trellises defines a set of valid next states of the decoder.

Each of the two or more component trellises of the decoder defines a set of valid inputs disjoint from all other component trellises in the two or more component trellises. The sets of valid inputs mirror the disjoint subsets of outputs generated by the two or more sets of connections of the encoder. For example, if a first set of connections produces a first subset of outputs, then a first component trellis defines a first set of valid inputs equivalent to the first subset of outputs.

The decoder may include a parameter that measures a distance between a received input and any possible valid input of the active component trellis of the two or more component trellises. The decoder may use these distances to identify insertion and deletion errors in a received sequence. The decoder may insert placeholders into (or remove bits from) the received sequence (or the decoded outputs) based on the insertion and deletion errors and locations of the insertion and deletion errors. The decoder may be designed to identify substitution errors. In the alternative, the described convolutional codes can be designed such that the substitution errors are transparent.

The described convolutional and trellis codes can be designed to fix errors or just detect errors. If more redundancy is added to the convolutional code, the convolutional and trellis codes can fix errors. To reduce redundancy the convolutional codes can be designed to only detect errors and allow classical error correction codes to correct the errors.

The convolutional and trellis codes described herein reduce the number of independent strings that need to be sequenced in order to achieve a particular reliability threshold by providing a method to detect insertion and deletion errors. Reducing the number of sequences required to read from a DNA storage system reduces the delay in the DNA storage system. After detecting insertions and deletions, the systems and methods can use classical error correcting codes to correct substitution errors and placeholders inserted by the decoder. The described convolutional and trellis codes can be designed based on a desired trade off between a number of independent strings to be sequenced and redundancy added in a coding subsystem.

The described systems and methods can detect insertion and deletion errors in the presence of substitution errors. They can detect multiple insertion and/or deletion errors happening in isolation or in clusters. As long as the distance between isolated or clustered insertion and/or deletion errors is more than a minimum distance, the described convolutional and trellis codes can detect all such events.

By detecting the insertion/deletion locations, the described systems and methods can adjust the location of code word symbols (for example, by inserting erasure symbols for deletions) and thereby prevent classical error correcting codes from breaking.

FIG. 1 illustrates a system 100 for detecting insertion and deletion errors in connection with writing to and reading from a dense storage medium 108. The system 100 can detect multiple insertion and deletion errors in a signal even when the signal also includes substitution errors. The system 100 may include a dense storage medium encoder 103 (which may include an electronic storage medium 102, an encoder 104, and a mapper 106), the dense storage medium 108, and a dense storage medium decoder 105 (which may include a sequencer 110, a decoder 112, and error correction codes 114).

The electronic storage medium 102 may be any material, device, or system in which electronic data can be stored and from which the electronic data can be retrieved. The electronic storage medium 102 may be a silicon-based storage medium. The electronic storage medium 102 may be a hard disk, an optical disk, flash memory, or tape. The electronic storage medium 102 may store the electronic data in strings of bits.

The encoder 104 receives a string of input bits and outputs a string of encoded bits. The encoder 104 may receive the input bits in k-bit length blocks and output an n-bit length encoded string for each k-bit length input block. The encoder 104 may encode a sequence of input vectors to produce a sequence of binary output vectors. Encoding may be a process that adds redundancy to the input bits to reduce a probability of errors or increases a level of acceptable noise in a channel. Thus, the encoded bits may include more information than is contained in the input bits. The encoder 104 may be a convolutional encoder. The encoder 104 is designed to enable detection of insertions and deletions in data read from the dense storage medium 108.

The encoder 104 includes two or more component convolutional codes.

Convolutional code can be marked by (n, k, K). For every k bits, a convolution code produces an output of n bits. K may be a constraint length of the convolutional code (which may represent a number of memories of the convolutional code). Because a convolutional code has memory, the current n-bit output depends not only on the value of the current block of k input bits but also on the previous K−1 blocks of k input bits.

A convolutional code may be a type of error-correcting code that generates parity symbols via a sliding application of a Boolean polynomial function to a data stream. A convolutional code may be characterized by a base code rate and a depth (or memory) of an encoder. The base code rate may be given as k/n, where k is the raw input data rate and n is the data rate of output channel encoded stream. The raw input data rate k is less than n because channel coding inserts redundancy in the input bits. The memory may be referred to as the "constraint length" K, where the output is a function of the current input as well as the previous K−1 inputs. The depth may also be given as the number of memory elements v in the polynomial or the maximum possible number of states of the encoder (typically: $2^v$).

A convolutional code may be a type of error-correction code in which (a) each k-bit information symbol (each k-bit string) to be encoded is transformed into an n-bit symbol, where n>k and (b) the transformation is a function of the last K information symbols, where K is the constraint length of the code.

Each of the two or more component convolutional codes of the encoder 104 may have a same n, k, and K. In this case, the overall rate of the encoder 104 may be defined by the ratio of k/n. In the alternative, each of the two or more component convolutional codes of the encoder 104 may have a different n and k (such as n1, n2, k1, and k2 where n1 is different from n2 and k1 is different from k2). In this case, the overall rate of the encoder 104 may be defined by the ratio of (k1+k2)/(n1+n2).

Each of the two or more component convolutional codes outputs symbols (strings of encoded bits) that are disjoint from other component convolutional codes in the two or more component convolutional codes. In other words, the two or more component convolutional codes are designed such that no component convolutional code produces a same string of encoded bits as any other component convolutional code. The two or more component convolutional codes together form a super code. Within the super code, the two or more component convolutional codes are time interlaced. In other words, for every k-bit input string, the encoder 104 rotates among the two or more component convolutional codes. The super code repeats, and the encoder 104 is defined by the super code.

As one example, the encoder 104 may include two component convolutional codes, component convolutional code 116a and component convolutional code 116b. The component convolutional code 116a and the component convolutional code 116b may each have an identical code rate and be designed to receive a same k-bit length input string and output a same n-bit length output string.

The component convolution code 116a is time interlaced with the component convolutional code 116b. For example, at time t1 (which may refer to a time of receiving a first k-bit length input string), the component convolutional code 116a is active, and at time t2 (which may refer to a time of receiving a second k-bit length input string), the component convolutional code 116b is active. This pattern repeats such that at time t3 the component convolutional code 116a is active, and at time t4 the component convolutional code 116b is active.

The encoder 104 may be designed to produce an output that is within a set of possible outputs. The component convolutional code 116a is designed to generate outputs within a first subset of the set of possible outputs, and the component convolutional code 116b is designed to generate outputs within a second subset of the set of possible outputs. The first subset is disjoint from the second subset. The first subset of outputs and the second subset of outputs may together include all outputs in the set of possible outputs of the encoder 104.

The mapper 106 may receive the encoded bits (outputs) from the encoder 104. The mapper 106 may map the encoded bits to one or more symbols and output the one or more symbols (which may be represented by output symbols 107 in FIG. 1). Each of the one or more symbols may be part of a symbol or code word alphabet. For example, if the dense storage medium 108 is synthetic DNA storage, then the one or more symbols may be one or more DNA bases and the set of possible DNA bases may form the symbol or code word alphabet. The mapper 106 may map outputs from the component convolutional code 116a to a first set of symbol combinations or sequences disjoint from a second set of symbol combinations or sequences to which the mapper 106 maps outputs from the component convolutional code 116b. For example, if the mapper 106 maps an output of the component convolutional code 116a to the DNA bases AGT, then the mapper 106 may be designed such that it does not map an output of the component convolutional code 116b to AGT.

The dense storage medium 108 may be any material, device, or system for storing information. The dense storage medium 108 may store information in a denser form than the electronic storage medium 102. The systems and methods described in this disclosure do not, however, require that the dense storage medium 108 store information in a denser form than the electronic storage medium 102.

Outputs from the mapper 106 (such as the output symbols 107) may be written to the dense storage medium 108. The dense storage medium 108 may be synthetic DNA storage. In DNA, there are four symbols in the code word alphabet. The four symbols are the four DNA bases of A, T, C, and G. When converted to electronic data, each of the four bases may be represented by two bits. The systems and methods described in this disclosure do not, however, require that the dense storage medium 108 be a synthetic DNA storage. It may be that the probability of going from one symbol to another symbol in DNA storage has equal probabilities. But even if the probabilities are different, the encoder 104 and the decoder 112 described could still allow for detection of multiple insertion and deletion errors in the presence of substitution errors.

Errors may occur in the process of writing information to the dense storage medium 108. These errors may include insertion and deletion errors. Consider an example in which the dense storage medium 108 is a synthetic DNA storage. The mapper 106 may output the following string of symbols: ATCGGCTA. But when the string of symbols is written to the DNA storage, one of the symbols may be lost such that the string written to the synthetic DNA storage is ATCGCTA. In the alternative, the string of symbols written to the DNA storage may include an additional symbol such that the string written to the synthetic DNA storage is ATACGGCTA.

The sequencer 110 may read information (which may be represented by read symbols 109 in FIG. 1) from the dense storage medium 108. The sequencer 110 may map the read information to a string of bits. For example, if the dense storage medium 108 is a synthetic DNA storage, the sequencer 110 may read DNA bases from the dense storage medium 108 and convert those DNA bases to bits that represent the DNA bases.

When the dense storage medium 108 is a synthetic DNA storage, sequencing a strand of synthetic DNA may be a slow process. Furthermore, technologies for reading synthesized DNA may result in a high probability that some insertions and/or deletions of symbols occur during sequencing. For example, a strand of synthetic DNA may include the following sequence: CGTA. But the sequencer 110 may erroneously read the sequence CTA or the sequence CGGTA. In the alternative, the sequencer 110 may read the sequence GTAA, which includes both an insertion and a deletion error. The sequencer 110 may also make substitution errors in addition to insertion and deletion errors. A substitution error may be an error in which a symbol is not inserted or deleted but is read incorrectly. For example, if a strand includes the sequence CGTA, a substitution error may be substituting the T with an A such that the sequencer 110 reads the sequence CGAA.

One way of handling the high probability that insertion and deletion errors will occur in sequencing synthesized DNA is to read the same sequence of synthesized DNA multiple times. Based on the probabilistic nature of insertions and deletions, a system can come to a statistical inference that a certain location in a sequence is the most probable place that an insertion or deletion occurred. Because sequencing is already slow, sequencing multiple times makes reading synthesized DNA even slower. The encoder 104 and the decoder 112 enable detection of insertion and deletion errors while reducing a number of reads necessary to meet a certain reliability threshold.

The decoder 112 receives bits and outputs decoded bits. The decoder 112 may receive n-bit length inputs. The n-bit length inputs may be part of a larger input stream. The decoder 112 may receive or process each n-bit length input block in the larger input stream sequentially. The decoder 112 may produce k-bit length decoded outputs. The decoder 112 may be a Viterbi decoder. The decoder 112 may receive bits from the sequencer 110. The bits may represent symbols stored in the dense storage medium 108. The decoder 112 is designed to enable detection of multiple insertions and deletions in data read from the dense storage medium 108. The decoder 112 may detect locations of insertions and deletions in data read from the dense storage medium 108. The decoder 112 may insert placeholder bits in decoded outputs in the locations where deletions in the data read from the dense storage medium 108 occurred. The decoder 112 may remove bits from the decoded outputs in the locations where insertions in the data read from the dense storage medium 108 occurred. The insertion and deletion errors may result from errors in writing and reading symbols to the dense storage medium 108.

The decoder 112 may use a trellis to decode received bits. The trellis may be a time-indexed graph that represents a given linear code. The trellis may be a directed, edge-labeled graph. The trellis may include columns and branches. Each column in the trellis may represent a set of possible states at a particular time. Branches may show valid transitions from states in one column to states in the next column. The decoder 112 may determine a most likely path through the trellis as part of decoding the received bits.

The decoder 112 includes two or more component trellis codes. Each of the two or more component trellis codes defines a set of branches and symbols (inputs) associated with each branch. Each of the two or more component trellis codes defines a set of valid inputs disjoint from all other component trellis codes in the two or more component trellis codes. The two or more component trellis codes together form a super trellis. Only one of the two or more component trellis codes is active at any given time (or for any particular input). Within the super trellis, the two or more component trellis codes are time interlaced. The super trellis repeats, and the decoder 112 is defined by the super trellis. The two or more component trellis codes may be designed based on the two or more component convolutional codes of the encoder 104. In the alternative, the two or more component convolutional codes may be designed based on the two or more component trellis codes.

As one example, the decoder 112 may include two component trellis codes, component trellis code 118a and component trellis code 118b. The component trellis code 118a is time interlaced with the component trellis code 118b. For example, at time t1 (which may represent a time at which the decoder 112 receives a first n-bit string of bits), the component trellis code 118a is active, and at time t2 (which may represent a time at which the decoder 112 receives a second n-bit string of bits), the component trellis code 118b is active. This pattern repeats such that at time t3 the component trellis code 118a is active, and at time t4 the component trellis code 118b is active.

The component trellis code 118a defines a first subset of valid inputs. The component trellis code 118b defines a second subset of valid inputs. The first subset is disjoint from the second subset. The first subset and the second subset may together define a set of valid inputs equivalent to the set of possible outputs of the encoder 104. The first subset of valid inputs of the component trellis code 118a may be equivalent to the first subset of outputs of the component convolutional code 116a. The second subset of valid inputs of the component trellis code 118a may be equivalent to the second subset of outputs of the convolutional code 116b.

The decoder 112 may include a distance parameter. The decoder 112 may measure a distance between received bits and any possible valid input defined by the currently active component trellis code. For example, if the component trellis code 118a is currently active, the decoder 112 may measure a distance between received bits and sequences contained in the first subset of valid inputs. The distance may be any choice of distance metrics such as an L1 (Manhattan) distance, an L2 distance, or similar distances.

The error correction codes 114 may receive a code word and detect and correct substitution errors in the code word. The code word may be defined by decoded bits output by the decoder 112. The code word may include multiple outputs of the decoder 112. The decoded bits in the code word may represent a string or sequence of symbols. For example, the code word may be a string of six bits and every two bits may represent a symbol (such as a DNA base). The symbols may be symbols used to store information in the dense storage medium 108. The error correction codes 114 may use an H' matrix. The error correction codes 114 may include low-density parity-check (LDPC).

The error correction codes 114 may require that the symbols be located in correct locations for the error correction codes 114 to detect and correct substitution errors. The error correction codes 114 may require that the code word be of a correct length for the error correction codes 114 to function properly. If a symbol has been deleted or inserted, the symbols may be misaligned (or the code word may have an incorrect length). For example, assume the code word should be a string of eight bits representing four symbols but the received code word is a string of six bits because one symbol is missing. Misalignment may cause the error correction codes 114 to not function properly. When the decoder 112 inserts placeholder bits where deletion errors have occurred (and removes excess bits where insertion errors have occurred), the error correction codes 114 may function properly. In that situation, the error correction codes 114 can correct the placeholder bits as a substitution error. Thus, the encoder 104 and decoder 112 together enable the error correction codes 114 to work even when insertion and deletion errors occur in the process of writing to and reading from the dense storage medium 108.

As noted above, the decoder 112 may identify insertion and deletion errors in received inputs and may identify locations in a bit stream of insertion and deletion errors. The decoder 112 may be designed to add bits to and remove bits from an output of the decoder 112 based on detecting insertion and deletion errors. The decoder 112 may be designed to add bits to and remove bits from particular locations based on the identified locations of insertion and deletion errors. In this way, the decoder 112 may modify one or more outputs of the decoder 112 such that symbols within code words received by the error correction codes 114 are in correct locations and the code words have correct lengths. The error correction codes 114 are then able to correct substitution errors (including placeholder bits) within the code words.

Figure 2A:
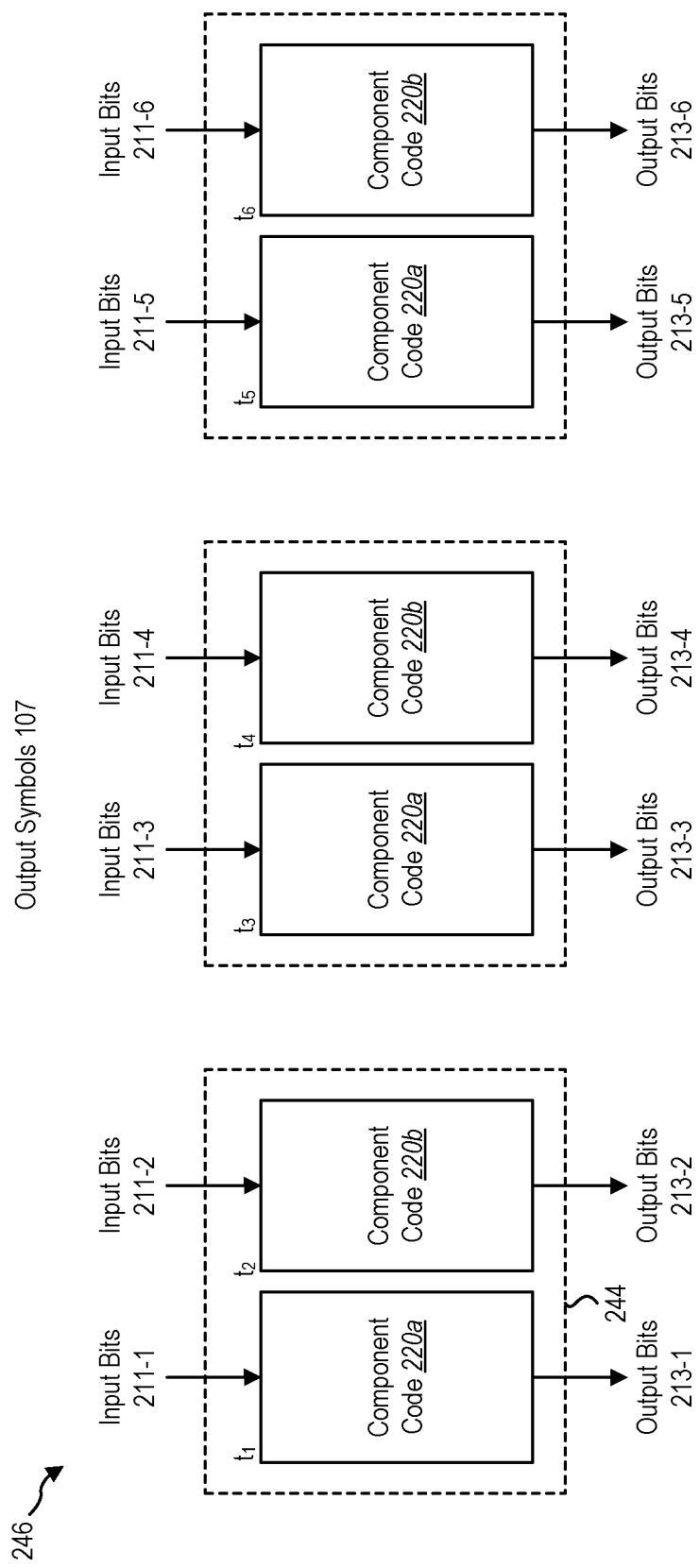
FIG. 2A illustrates an example code consisting of two component codes that enables detection of multiple insertion and deletion errors in a signal.

FIG. 2A illustrates an example code 246. The code 246 includes component code 220a and component code 220b. The component code 220a may receive input bits and provide output bits. The component code 220b may receive input bits and provide output bits. The input bits may be retrieved from an electronic storage, such as the electronic storage medium 102. The input bits may have a length of k bits, and the output bits may have a length of n bits. The output bits may be encoded bits. The output bits may represent one or more symbols or may be mapped to one or more symbols. For example, every two bits of the output bits may represent a DNA base. The component code 220a may be a convolutional code or a trellis code. The component code 220b may be a convolutional code or a trellis code. It may be possible to describe the code 246 as a trellis. The component code 220a and the component code 220b may share convolutional code memories. The component code 220a and the component code 220b may together form a super code 244. The super code 244 may define the code 246. The code 246 may be used in an encoder, such as the encoder 104. The code 246 may be used to design a trellis for use in a decoder, such as the decoder 112.

Within the super code 244, the component code 220a and the component code 220b are time interlaced. The component code 220a may apply at time t1 (which may be a first time when the code 246 receives a first input of k bits), and the component code 220b may apply at time t2 (which may be a second time after the first time when the code 246 receives a second input of k bits). In other words, the component code 220a may receive a first input (which may be represented by input bits 211-1 in FIG. 2A) received by the code 246 at time t1, and the component code 220b may receive a second input (which may be represented by input bits 211-2 in FIG. 2A) received by the code 246 at time t2. The super code 244 may repeat. For example, the code 246 may receive a third input (which may be represented by input bits 211-3) at time t3, a fourth input (which may be represented by input bits 211-4) at time t4, a fifth input (which may be represented by input bits 211-5) at time t5, and a sixth input (which may be represented by input bits 211-6) at time t6. The component code 220a may receive the third input at time t3 and the fifth input at time t5. The component code 220b may receive the fourth input at time t4 and the sixth input at time t6.

The component code 220a and the component code 220b are designed such that the component code 220a produces outputs that are disjoint from outputs that the component code 220b produces. FIG. 2B illustrates a set of possible outputs 222 that the component code 220a and the component code 220b can produce. The set of possible outputs 222 may be divided into subset 224a and subset 224b. The subset 224a may include a first subset of outputs in the set of possible outputs 222, and the subset 224b may include a second subset of outputs in the set of possible outputs 222. The subset 224a and the subset 224b are disjoint. In other words, none of the outputs in the subset 224a are included in the subset 224b and none of the outputs in the subset 224b are included in the subset 224a. The component code 220a may be designed to produce outputs in the subset 224a, and the component code 220b may be designed to produce outputs in the subset 224b.

For example, after receiving the input bits 211-1, the component code 220a may produce output bits 213-1. The output bits 213-1 are within the subset 224a. After receiving the input bits 211-2, the component code 220b may produce output bits 213-2. The output bits 213-2 are within the subset 224b. After receiving the input bits 211-3, the component code 220a may produce output bits 213-3. The output bits 213-3 are within the subset 224a. After receiving the input bits 211-4, the component code 220b may produce output bits 213-4. The output bits 213-4 are within the subset 224b. After receiving the input bits 211-5, the component code 220a may produce output bits 213-5. The output bits 213-5 are within the subset 224a. After receiving the input bits 211-6, the component code 220b may produce output bits 213-6. The output bits 213-6 are within the subset 224b.

FIG. 3A illustrates an example code 346. The code 346 includes component code 320a, component code 320b, and component code 320c. Each of the component code 320a, the component code 320b, and the component code 320c may receive input bits and produce output bits. The output bits may represent one or more symbols. Each of the component code 320a, the component code 320b, and the component code 320c may be a convolutional code. The component code 320a, the component code 320b, and the component code 320c may together form a super code 344. The super code 344 may define the code 346. The code 346 may be used in an encoder. The code 346 may be used to design a trellis for use in a decoder.

Within the super code 344, the component code 320a, the component code 320b, and the component code 320c are time interlaced. The component code 320a may apply at time t1, the component code 320b may apply at time t2, and the component code 320c may apply at time t3. In other words, the component code 320a may receive a first input (which may be represented by input bits 311-1) received by the code 346 at time t1 (or the code 346 may apply the component code 320a to the first input received at time t1), the component code 320b may receive a second input (which may be represented by input bits 311-2) received by the code 346 at time t2 (or the code 346 may apply the component code 320b to the second input received at time t2), and the component code 320c may receive a third input (which may be represented by input bits 311-3) received by the code 346 at time t3 (or the code 346 may apply the component code 320c to the third input received at time t3). The super code 344 may repeat. For example, the code 346 may receive a fourth input (which may be represented by input bits 311-4) at time t4, a fifth input at time t5 (which may be represented by input bits 311-5), a sixth input at time t6 (which may be represented by input bits 311-6), a seventh input at time t7 (which may be represented by input bits 311-7), an eighth input (which may be represented by input bits 311-8) at time t8, and a ninth input at time t9 (which may be represented by input bits 311-9). The component code 320a may receive the fourth input at time t4 and the seventh input at time t7. The component code 320b may receive the fifth input at time t5 and the eighth input at time t8. The component code 320c may receive the sixth input at time t6 and the ninth input at time t9.

Figure 3B:
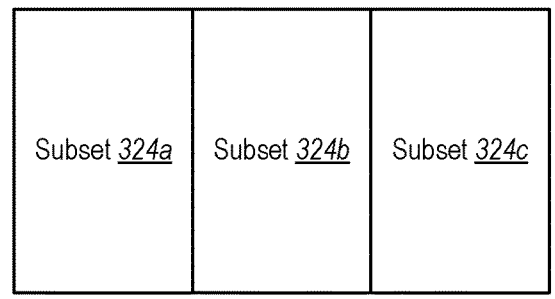
FIG. 3B illustrates an example division of a set of possible outputs into three subsets in order to enable detection of multiple insertion and deletion errors in a signal.

The component code 320a, the component code 320b, and the component code 320c are designed such that they produce outputs disjoint from each other. The component code 320a produces outputs that are disjoint from outputs that the component code 320b and the component code 320c produce. The component code 320b produces outputs that are disjoint from outputs that the component code 320a and the component code 320c produce. The component code 320c produces outputs that are disjoint from outputs that the component code 320a and the component code 320b produce. FIG. 3B illustrates a set of possible outputs 322 that the component code 320a, the component code 320b, and the component code 320c can produce. The set of possible outputs 322 may be divided into subset 324a, subset 324b, and subset 324c. The subset 324a, the subset 324b, and the subset 324c may be disjoint. In other words, none of the outputs in the subset 324a are included in the subset 324b or the subset 324c, none of the outputs in the subset 324b are included in the subset 324a or the subset 324c, and none of the outputs in the subset 324c are included in the subset 324a or the subset 324b. The component code 320a may be designed to produce outputs in the subset 324a, the component code 320b may be designed to produce outputs in the subset 324b, and the component code 320c may be designed to produce outputs in the subset 324c.

For example, after receiving the input bits 311-1, the component code 320a may produce output bits 313-1. The output bits 313-1 are within the subset 324a. After receiving the input bits 311-2, the component code 320b may produce output bits 313-2. The output bits 313-2 are within the subset 324b. After receiving the input bits 311-3, the component code 320c may produce output bits 313-3. The output bits 313-3 are within the subset 324c. After receiving the input bits 311-4, the component code 320a may produce output bits 313-4. The output bits 313-4 are within the subset 324a. After receiving the input bits 311-5, the component code 320b may produce output bits 313-5. The output bits 313-5 are within the subset 324b. After receiving the input bits 311-6, the component code 320c may produce output bits 313-6. The output bits 313-6 are within the subset 324c. After receiving the input bits 311-7, the component code 320a may produce output bits 313-7. The output bits 313-7 are within the subset 324a. After receiving the input bits 311-8, the component code 320b may produce output bits 313-8. The output bits 313-8 are within the subset 324b. After receiving the input bits 311-9, the component code 320c may produce output bits 313-9. The output bits 313-9 are within the subset 324c.

Figure 4A:
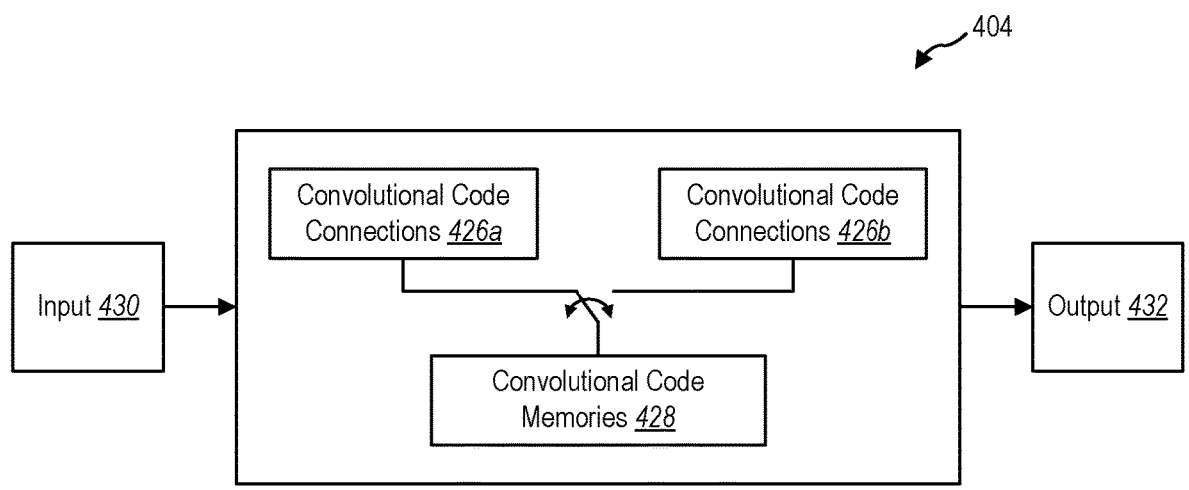
FIG. 4A illustrates an example encoder that includes two sets of convolutional code connections and one set of convolutional code memories shared by the two sets of convolutional code connections.

FIG. 4A illustrates an example encoder 404. The encoder 404 may be used in the system 100. The encoder 404 may be designed to enable detection of multiple insertion and deletion errors. The encoder 404 may be designed based on two component convolutional codes.

The encoder 404 receives an input 430 and produces an output 432. The input 430 may be a string of k bits, and the output 432 may be a string of n bits. The output 432 includes more bits than the input 430. The ratio of k/n may define a code rate of the encoder 404. The output 432 may include error-correcting information. The input 430 may be obtained from an electronic storage medium, such as the electronic storage medium 102. The input 430 may be one of a set of inputs.

The encoder 404 includes convolutional code connections 426a, convolutional code connections 426b, and convolutional code memories 428. The encoder 404 may determine the output 432 based on the input 430, the convolutional code memories 428, and one of the convolutional code connections 426a or the convolutional code connections 426b. Although the encoder 404 is shown with two sets of convolutional code connections, in other designs, an encoder may include more than two sets of convolutional code connections.

The convolutional code memories 428 may include one or more memories. Each of the memories may be a single bit. Each of the memories may take the value "0" or "1." Contents of the memories represent a state of the encoder 404. For example, assume the convolutional code memories 428 include two memories. Assume a first memory has a value of 0 and a second memory has a value of 1. The state of the encoder 404 in that case is 01. The encoder 404 may modify the contents of the memories in response to receiving the input 430.

The convolutional code connections 426a, 426b share the convolutional code memories 428. The convolutional code memories 428 may connect to only one of the convolutional code connections 426a, 426b at one time. The encoder 404 may switch between the convolutional code connections 426a, 426b with each received input. For example, at a time t1 (which may be a time at which the encoder 404 receives a first input), the convolutional code memories 428 may connect to the convolutional code connections 426a and not the convolutional code connections 426b. Then, at time t2 (which may be a time after time t1 at which the encoder 404 receives a second input), the convolutional code memories 428 may connect to the convolutional code connections 426b and not to the convolutional code connections 426a.

The convolutional code connections 426a, 426b may be feedback or network connections between and among the convolutional code memories 428 and the input 430. The convolutional code connections 426a, 426b may be designed such that when the convolutional code memories 428 are connected to the convolutional code connections 426a, the encoder 404 produces outputs that are disjoint from outputs produced by the encoder 404 when the convolutional code memories 428 are connected to the convolutional code connections 426b. The convolutional code connections 426a, 426b may be designed based on component convolutional codes, such as the component convolutional codes 116a, 116b or the component codes 220a, 220b.

The encoder 404 may receive the input 430. The input 430 may be a string of bits. The string of bits may represent data that is to be encoded and stored in a dense storage medium, such as a DNA storage. The input 430 may be received at a particular time (such as at time t1). The input 430 may be part of a set of inputs. The encoder 404 may receive each input in the set of inputs one at a time or process each input in the set of inputs one at a time. For example, the encoder 404 may receive (or process) a first input in a set of inputs at a first time and may receive (or process) a second input in the set of inputs at a second time after the first time. For each input, the encoder 404 may generate an output.

The encoder 404 may produce the output 432 in response to receiving the input 430. The output 432 may be a string of bits. The output 432 may represent one or more symbols or may be mapped (such as by the mapper 106) to one or more symbols. The one or more symbols may be written to a dense storage medium, such as a synthetic DNA storage. The encoder 404 may determine the output 432 based on the input 430, current contents of the convolutional code memories 428, and the currently applicable convolutional code connections (either the convolutional code connections 426a or the convolutional code connections 426b).

In response to receiving an input (such as the input 430), the encoder 404 may determine values of the convolutional code memories 428. The convolutional code memories 428 may represent a current state of the encoder 404. The encoder 404 may determine values for the convolutional code memories 428 based on the input 430, current contents of the convolutional code memories 428 (i.e., a current state of the encoder 404), and the currently applicable convolutional code connections (either the convolutional code connections 426a or the convolutional code connections 426b).

Figure 4B:
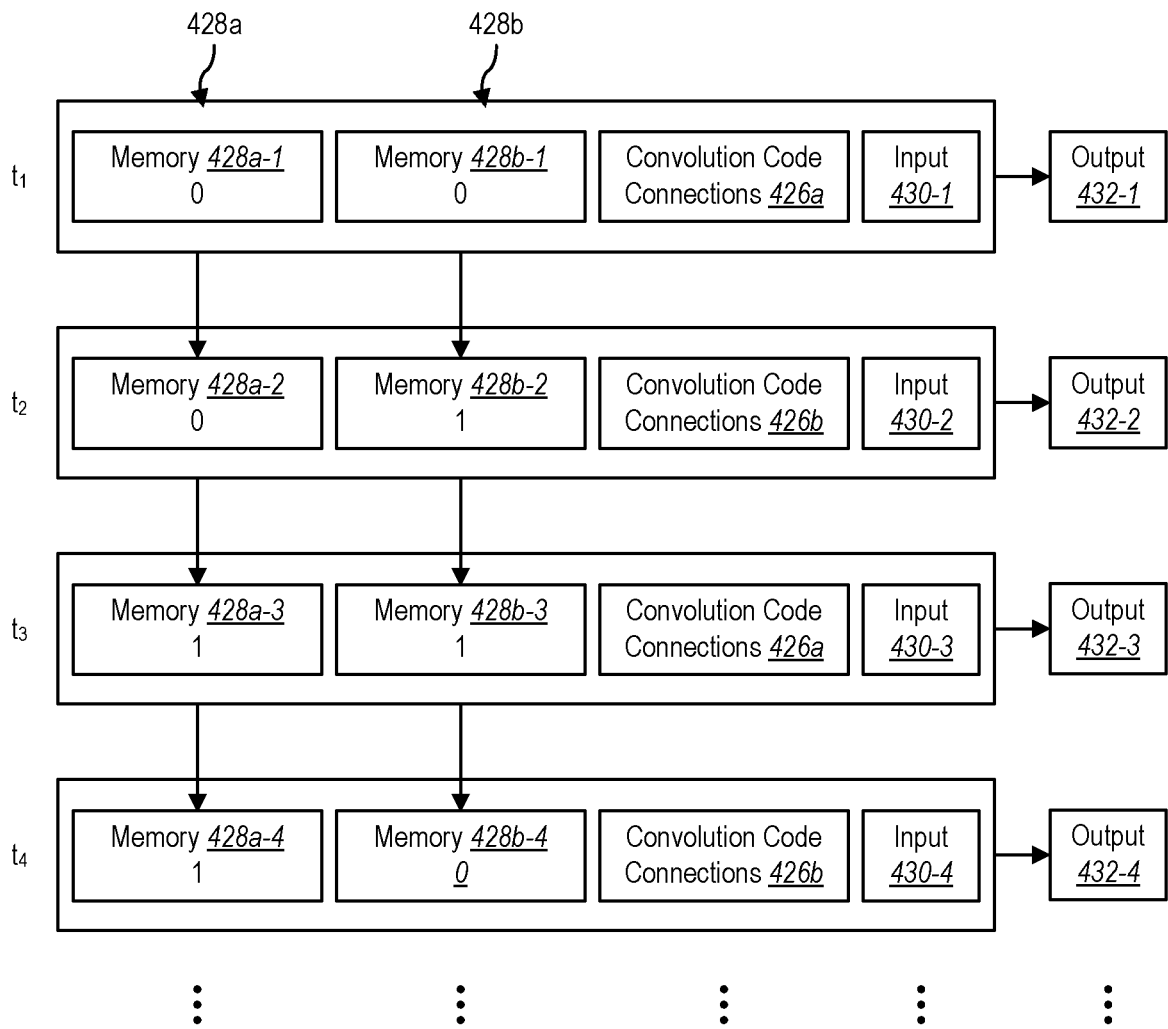
FIG. 4B illustrates an example sequence of an encoder receiving inputs and producing outputs based on the inputs, convolutional code memories, and convolutional code connections.

FIG. 4B illustrates one example of the encoder 404 receiving inputs and producing outputs. In this example, the encoder 404 receives (or processes) inputs at four different times, t1, t2, t3, and t4. In this example, the convolutional code memories 428 may include two memories, memory 428a and memory 428b.

At time t1, the encoder 404 may receive input 430-1 and the convolutional code connections 426a may be connected to the convolutional code memories 428. Memory 428a-1 may represent a current content of the memory 428a at the time t1, and memory 428b-1 may represent a current content of the memory 428b at the time t1. For example, the memory 428a-1 may have a value of "0," and the memory 428b-1 may have a value of "0." In response to receiving the input 430-1, the encoder 404 may produce output 432-1. The encoder 404 may determine the output 432-1 based on the memory 428a-1, the memory 428b-1, the input 430-1, and the convolutional code connections 426a. The convolutional code connections 426a may be designed such that the convolutional code connections 426a produce only outputs within a first subset of possible outputs. The output 432-1 may be within the first subset of possible outputs.

The encoder 404 may determine new values of the memory 428a-1 and the memory 428b-1 based on the input 430-1, the memory 428a-1, the memory 428b-1, and the convolutional code connections 426a. The new value of the memory 428a-1 may be represented by memory 428a-2, and the new value of the memory 428b-1 may be represented by memory 428b-2. The encoder 404 may determine the value of the memory 428a-2 to be "0" based on the input 430-1, the convolutional connections 426a, the memory 428a-1, and the memory 428b-1. The encoder 404 may determine the value of the memory 428b-2 to be "1" based on the input 430-1, the convolutional connections 426a, the memory 428a-1, and the memory 428b-1.

At time t2, the encoder 404 may receive input 430-2, and the convolutional code connections 426b may be connected to the convolutional code memories 428. The memory 428a-2 may represent a current content of the memory 428a at the time t2, and the memory 428b-2 may represent a current content of the memory 428b at the time t2. The memory 428a-2 may have a value of "0," and the memory 428b-2 may have a value of "1." In response to receiving the input 430-2, the encoder 404 may produce output 432-2. The encoder 404 may determine the output 432-2 based on the memory 428a-2, the memory 428b-2, the input 430-2, and the convolutional code connections 426b. The output 432-2 is different from the output 432-1. The convolutional code connections 426b may be designed such that the convolutional code connections 426b produce only outputs within a second subset of the possible outputs. The output 432-2 may be within the second subset of the possible outputs. The second subset may be disjoint from the first subset.

The encoder 404 may determine new values of the memory 428a and the memory 428b based on the input 430-2, the memory 428a-2, the memory 428b-2, and the convolutional code connections 426b. The new value of the memory 428a may be represented by memory 428a-3, and the new value of the memory 428b may be represented by memory 428b-3. The encoder 404 may determine the value of the memory 428a-3 to be "1" based on the input 430-2, the convolutional connections 426b, the memory 428a-2, and the memory 428b-2. The encoder 404 may determine the value of the memory 428b-3 to be "1" based on the input 430-2, the convolutional connections 426b, the memory 428a-2, and the memory 428b-2.

At time t3, the encoder 404 may receive input 430-3, and the convolutional code connections 426a may be connected to the convolutional code memories 428. The memory 428a-3 may represent a current content of the memory 428a at the time t3, and the memory 428b-3 may represent a current content of the memory 428b at the time t3. The memory 428a-3 may have a value of "1," and the memory 428b-3 may have a value of "1." In response to receiving the input 430-3, the encoder 404 may produce output 432-3. The encoder 404 may determine the output 432-3 based on the memory 428a-3, the memory 428b-3, the input 430-3, and the convolutional code connections 426a. The output 432-3 is different from the output 432-2. The output 432-3 is within the first subset of the possible outputs.

The encoder 404 may determine new values of the memory 428a and the memory 428b based on the input 430-3, the memory 428a-3, the memory 428b-3, and the convolutional code connections 426a. The new value of the memory 428a may be represented by memory 428a-4, and the new value of the memory 428b may be represented by memory 428b-4. The encoder 404 may determine the value of the memory 428a-4 to be "1" based on the input 430-3, the convolutional connections 426a, the memory 428a-3, and the memory 428b-3. The encoder 404 may determine the value of the memory 428b-4 to be "0" based on the input 430-3, the convolutional connections 426a, the memory 428a-3, and the memory 428b-3.

At time t4, the encoder 404 may receive input 430-4, and the convolutional code connections 426b may be connected to the convolutional code memories 428. The memory 428a-4 may represent a current content of the memory 428a at the time t4, and the memory 428b-4 may represent a current content of the memory 428b at the time t4. The memory 428a-4 may have a value of "1," and the memory 428b-4 may have a value of "0." In response to receiving the input 430-4, the encoder 404 may produce output 432-4. The encoder/decoder _ may determine the output 432-4 based on the memory 428a-4, the memory 428b-4, the input 430-4, and the convolutional code connections 426b. The output 432-4 is different from the output 432-3 and the output 432-1. The output 432-4 is within the second subset of the possible outputs.

Figures 5A, 5B:
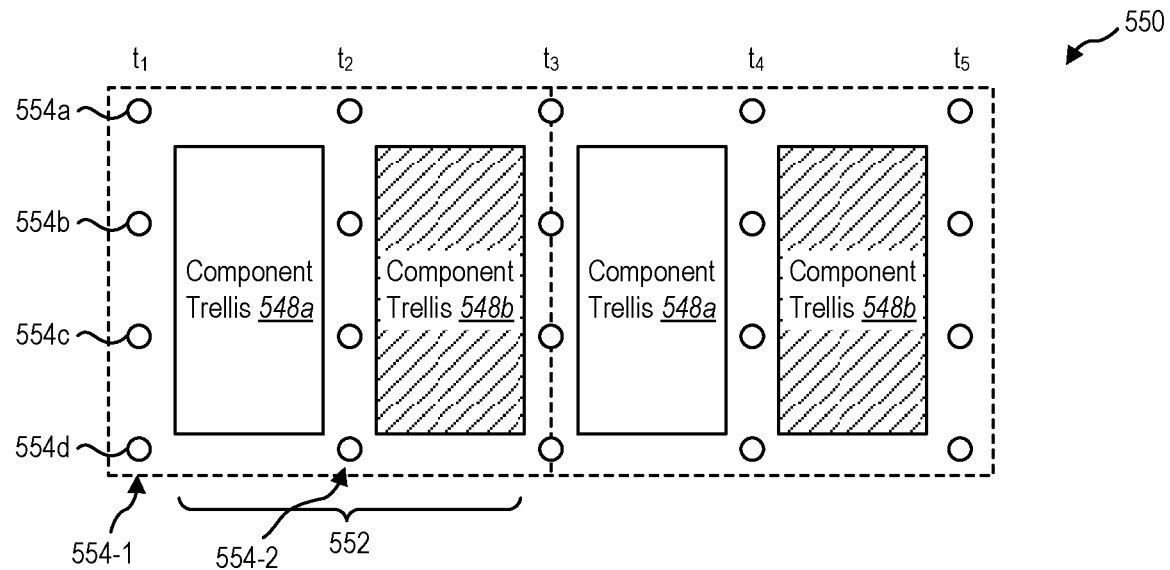
FIG. 5A illustrates an example trellis that includes two component trellises.
FIG. 5B illustrates example code words that a decoder may receive.

FIG. 5A illustrates an example trellis 550. The trellis 550 may be used by a decoder (such as the decoder 112) to decode an encoded input and may enable identifying insertion and deletion errors in received inputs. The trellis 550 may designed based on a convolutional code (such as the code 246) used in an encoder.

The trellis 550 may be divided into two groups. From time t1 to time t2 and from time t3 to time t4 may be a first group. From time t2 to time t3 and from time t4 to time t5 may be a second group. A different set of equations may apply in the first group than applies in the second group. Furthermore, a different set of inputs may be valid in the first group than are valid in the second group. The two groups may share a common set of memories.

The trellis 550 includes component trellis 548a and component trellis 548b. The component trellis 548a may apply in the first group, and the component trellis 548b may apply in the second group. The component trellis 548a and the component trellis 548b may share a common set of memories.

The trellis 550 may receive input bits and produce output bits. The input bits may represent one or more symbols. For example, a sequencer (such as the sequencer 110) may sequence a set of one or more DNA bases from a synthetic DNA storage and covert the one or more symbols to a string of bits. The output bits may be a best estimation by the trellis 550 as to the contents of a previously encoded message. The trellis 550 may use only one of the component trellis 548a or the component trellis 548b with respect to any particular input in determining an output. The trellis 550 may switch between the component trellis 548a and the component trellis 548b.

The output bits (or a collection of the output bits) may be provided to error correction codes, such as the error correction codes 114. The error correction codes may fix substitution errors in the output bits. The component trellis 548a and the component trellis 548b may together form a super trellis 552. Within the super trellis 552, the component trellis 548a and the component trellis 548b may be time interlaced. The super trellis 552 may repeat and may define the trellis 550. Although the trellis 550 is shown with two component trellises, in other designs, a trellis may include more than two component trellises.

The component trellis 548a may define a first set of valid inputs. The component trellis 548b may define a second set of valid inputs. The first set of valid inputs may be disjoint from the second set of valid inputs. The first set of valid inputs may be identical to a first subset of outputs of a first component convolutional code (such as the component convolutional code 116a or the component code 220a) in an encoder. The second set of valid inputs may be identical to a second subset of outputs of a second component convolution code (such as the component convolutional code 116b or the component code 220b) in the encoder.

The trellis 550 may include states 554a, 554b, 554c, 554d. The states 554a, 554b, 554c, 554d may be possible states of the trellis 550. At each time (t1, t2, t3, t4, etc.), the trellis 550 may have one of the states 554a, 554b, 554c, 554d. Although the trellis 550 in FIG. 5A includes four states, in other designs, a trellis can have more or fewer states. The number of states of a trellis may be based on a number of memories of an encoder and a decoder. The more memories, the greater the complexity of the encoder and the decoder. The number of states of a trellis may depend on a number of memories of an encoder and decoder. Branches (not shown) may define valid transitions from states of a first time (such as states 554-1 at time t1) to states at a second time (such as states 554-2 at time t2).

Within the super trellis 552, the component trellis 548a and the component trellis 548b are time interlaced. At time t1 (which may be a time at which the trellis 550 receives or processes a first input), the component trellis 548a may define branches and symbols (inputs) associated with each branch. The branches may define valid state transitions at time t1. In other words, the component trellis 548a may define to which state the trellis 550 should transition based on the first input. The component trellis 548a may also determine probabilistically a most likely output based on a received input, a current state of the trellis 550 at time t1, and the branches defined in the component trellis 548a. At time t2 (which may be a time at which the trellis 550 receives or processes a second input after receiving the first input), the component trellis 548b may define branches and symbols (inputs) associated with each branch. The branches may define valid state transitions at time t2. In other words, the component trellis 548b may define to which state the trellis 550 should transition based on the second input. The component trellis 548b may also determine probabilistically a most likely output based on a received input, a current state of the trellis 550 at time t2, and the branches defined in the component trellis 548b. At time t3, the component trellis 548a may again define the branches and the symbols associated with each branch. At time t4, the component trellis 548b may again define the branches and the symbols associated with each branch.

FIG. 5B illustrates example code words 534a, 534b, 534c.

The code word 534a may be an output of a decoder, such as the decoder 112. In the alternative, the code word 534a may include a collection of outputs from a decoder. The code word 534a may include symbols 536a, 536b, 536c, 536d, 536e, 536f, 536g. Each of the symbols 536a, 536b, 536c, 536d, 536e, 536f, 536g may be represented by one or more bits. The code word 534a may represent a string of bits that was encoded by an encoder, written to a storage medium, read from the storage medium, and decoded by a decoder. The code word 534a may be input into error correction codes. The code word 534a may not include any insertion or deletion errors.

The code word 534b illustrates an example of a deletion error occurring in the code word 534a. As with the code word 534a, the code word 534b includes the symbols 536a, 536b, 536d, 536e, 536f, 536g. The code word 534b does not, however, include the symbol 536c. The code word 534b may not include the symbol 536c because a read error occurred in reading symbols from a storage medium. In the alternative, the code word 534b may not include the symbol 536c because a write error occurred in writing symbols to the storage medium. Because the code word 534b does not include the symbol 536c, error correction codes may not work on the code word 534b.

The code word 534c illustrates an example of how a decoder as described herein may modify the code word 534b such that error correction codes work on the code word 534c. The code word 534c may include symbols 536a, 536b, 536d, 536e, 536f, 536g. The code word 534c may also include placeholder 538. The placeholder 538 may include a same number of bits as the symbol 536c. The placeholder 538 may, however, include bits different from the symbol 536c. The placeholder 538 may be located in a same location as the symbol 536c. Because the code word 534c includes the placeholder 538, error correction codes may work on the code word 534c.

A decoder as described herein may detect that a deletion error has occurred in between the symbol 536b and the symbol 536d in the code word 534b. The decoder may therefore input the placeholder 538 in between the symbol 536b and the symbol 536d. The decoder may determine a value of the placeholder 538 based on what symbols are valid inputs for a location of the placeholder 538. The decoder may select the value of the placeholder 538 to be a symbol that is valid for the location of the placeholder 538. Inserting the placeholder 538 may allow error correction codes to treat the placeholder 538 as a substitution error and correct the placeholder 538 as a substitution error.

Figure 6:
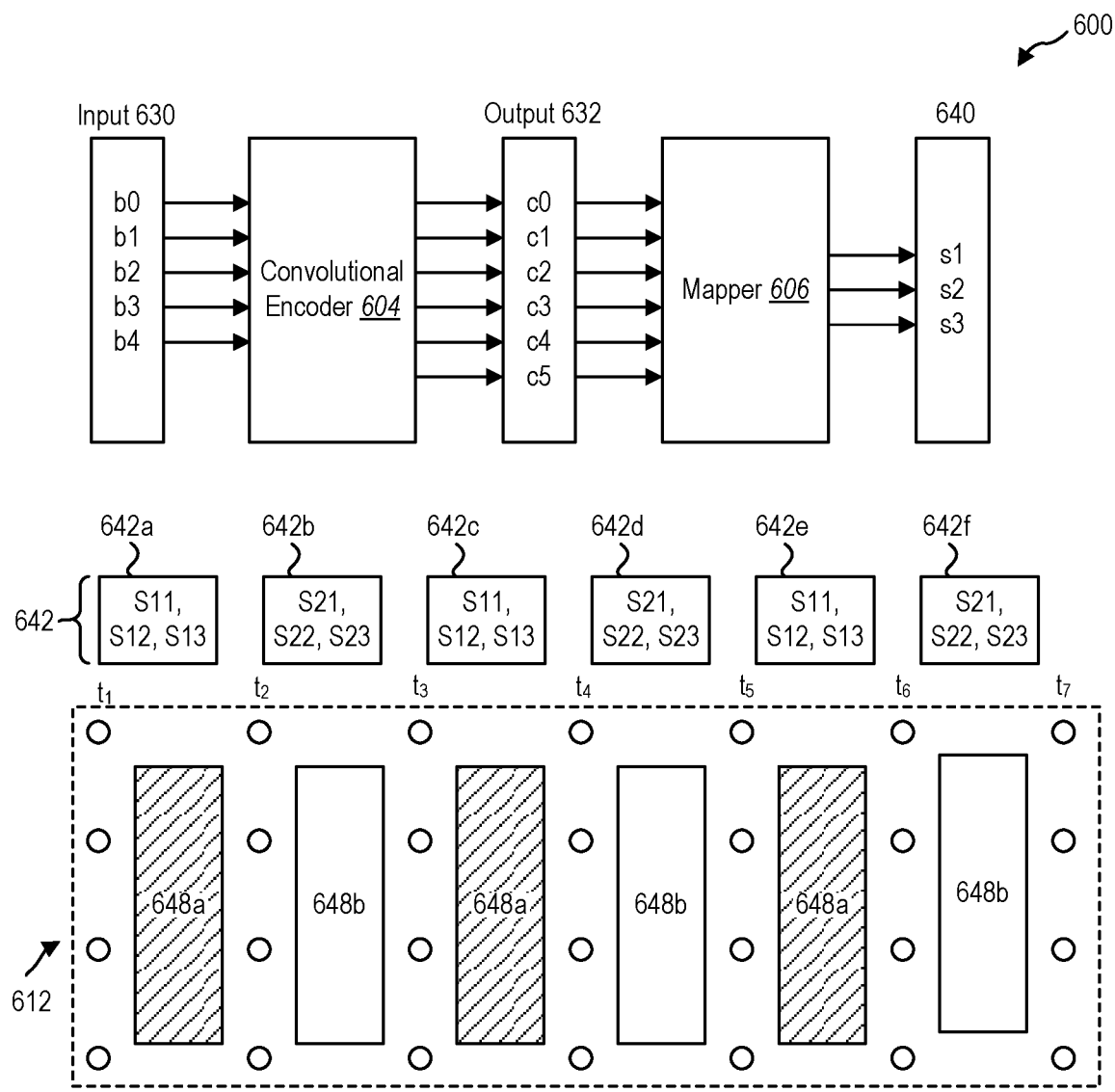
FIG. 6 illustrates an example system for detecting multiple insertion and deletion errors in the presence of substitution errors in inputs received from DNA storage.

FIG. 6 illustrates an example system 600 for detecting multiple insertion and deletion errors in the presence of substitution errors. The system 600 may include a convolutional encoder 604, a mapper 606, and a decoder 612.

The convolutional encoder 604 may receive inputs and produce encoded outputs based on the inputs and two component convolutional codes (a first component convolutional code and a second component convolutional code) included in the convolutional encoder 604. The first component convolutional code may be the component convolutional code 116*a* or the component code 220*a*. The second component convolutional code may be the component convolutional code 116*b* or the component code 220*b*.

Each of the two component convolutional codes may include a set of convolutional connections. The first component convolutional code may include a first set of convolutional connections (which may be the convolutional code connections 426*a*), and the second component convolutional code may include a second set of convolutional connections (which may be the convolutional code connections 426*b*). The first component convolutional code and the second component convolutional code may share convolutional memories (which may be the convolutional code memories 428). Only one of the first set of convolutional connections and the second set of convolutional connections may connect to the convolutional memories at one time or for processing a particular input). The convolutional encoder 604 may include any of the features or characteristics of the encoder 104 or the encoder 404.

The convolutional encoder 604 may produce outputs within a set of possible outputs. The first component convolutional code may produce outputs within a first set of the set of possible outputs, and the second component convolutional code may produce outputs within a second set of the set of possible outputs. The first set and the second set are disjoint.

The convolutional encoder 604 may receive input 630. The input 630 may include bits b0, b1, b2, b3, b4. Each of the bits b0, b1, b2, b3, b4 may have a value of 0 or 1. The input 630 may be read from an electronic storage medium (such as the electronic storage medium 102). The convolutional encoder 604 may produce output 632. The output 632 may include bits c0, c1, c2, c3, c4, c5, c6. Each of the bits c0, c1, c2, c3, c4, c5, c6 may have a value of 0 or 1. The convolutional encoder 604 determines the output 632 based on the input 630, current contents of the convolutional memories (which represent a current state of the convolutional encoder 604), and the set of convolutional connections currently connected to the convolutional memories (either the first set of convolutional connections or the second set of convolutional connections). For each input that the convolutional encoder 604 receives, the convolutional encoder 604 switches between the first set of convolutional connections and the second set of convolutional connections. The convolutional encoder 604 applies only one of the first set of convolutional connections or the second set of convolutional connections to any given input in determining an output.

The mapper 606 receives the output 632 and produces output 640. The mapper 606 may map the bits c0, c1, c2, c3, c4, c5 to a set of symbols. The output 640 may include symbols S1, S2, S3. The symbols S1, S2, S3 may each be one of the DNA bases. When the symbols S1, S2, S3 are each one of the DNA bases, S1, S2, and S3 may build a cubic with 64 points in a space. These 64 points are partitioned into two sets of 32 disjoint sets, a first subset and a second subset. The first set of convolutional connections may be designed to produce outputs that map only to points in the first subset, and the second set of convolutional connections may be designed to produce outputs that map only to points in the second subset.

Although FIG. 6 shows only the input 630 and the output 640, the convolutional encoder 604 may receive multiple inputs leading to multiple outputs from the mapper 606.

The system 600 may write the output 640 to a dense storage medium (such as the dense storage medium 108). The dense storage medium may be a synthetic DNA storage.

The decoder 612 may receive inputs. The inputs may be strings of bits. The strings of bits may represent symbols read from the dense storage medium, such as the synthetic DNA storage. For each received input, the decoder 612 may produce an output and determine a distance. The output may be a decoded version of the input. If there are no errors in the received input, the decoder 612 will output bits identical to bits input into the convolutional encoder 604. The distance may be a distance between the received input and any possible valid input defined in an applicable component trellis code. The decoder 612 may be a Viterbi decoder. The distance may be a L1 (Manhattan) distance. The distance may be based on:

$$d(Si, Yi) = d(S1i, Y1i) + d(S2i, Y2i) + d(S3i, Y3i)$$

Where, $$d(Ski, Yki) = \begin{cases} 0; & Ski = Yki \\ 1; & \text{Otherwise} \end{cases}$$

The decoder 612 may include two component trellis codes, a first trellis code 648*a* and a second trellis code 648*b*. The first trellis code 648*a* may recognize as valid only sequences that included in the first subset. The second trellis code 648*b* may recognize as valid only sequences included in the second subset.

By way of example, the decoder 612 may receive inputs 642. The decoder 612 may receive input 642*a* at time t1, input 642*b* at time t2, input 642*c* at time t3, input 642*d* at time t4, input 642*e* at time t5, and input 642*f* at time t6.

The inputs 642*a*, 642*c*, 642*e* may include symbols S11, S12, S13. The sequence S11, S12, S13 may be in the first subset. The inputs 642*b*, 642*d*, 642*f* may include symbols S21, S22, S23. The sequence S21, S22, S23 may be included in the second subset.

At times t1, t3, and t5, the decoder 612 may apply the first trellis code 648*a*. At times t2, t4, and t6, the decoder 612 may apply the second trellis code 648*b*. Because the inputs 642*a*, 642*c*, 642*e* are sequences from the first subset and the inputs 642*b*, 642*d*, 642*f* are sequences from the second subset, the decoder 612 may determine that no insertion or deletion errors have occurred in the inputs 642.

Assume, however, that the symbol S13 in the input 642*a* is deleted and all the subsequent symbols slide up one place such that the symbol S21 from the input 642*b* is now included in the input 642*a*, the symbol S11 from the input 642*c* is not included in the input 642*b*, the symbol S21 from the input 642*d* is now in the input 642*c*, the symbol S11 from the input 642*e* is now in the input 642*d*, and the symbol S21 from the input 642*f* is now in the input 642*e*. Assume that the sequence S11, S12, S21 is not a sequence in the first subset and that the sequence S22, S23, S11 is not a sequence in the second subset. The decoder 612 may determine that a non-zero distance exists between each of the inputs 642 and any possible valid sequence. The decoder 612 may therefore determine that a deletion error has occurred and determine a location of the deletion error. The decoder 612 may insert a placeholder at a location of the deletion error. In this example, the decoder 612 may insert a placeholder in the input 642*a* where the symbol S13 is shown in FIG. 6.

Alternatively, the decoder 612 may insert a placeholder set of decoded bits in a decoded output where decoded bits for the symbol S13 would have been.

The decoder 612 may provide decoded bits to error correction codes (such as LDPC) that can correction substitution errors in the decoded bits.

Figure 7:
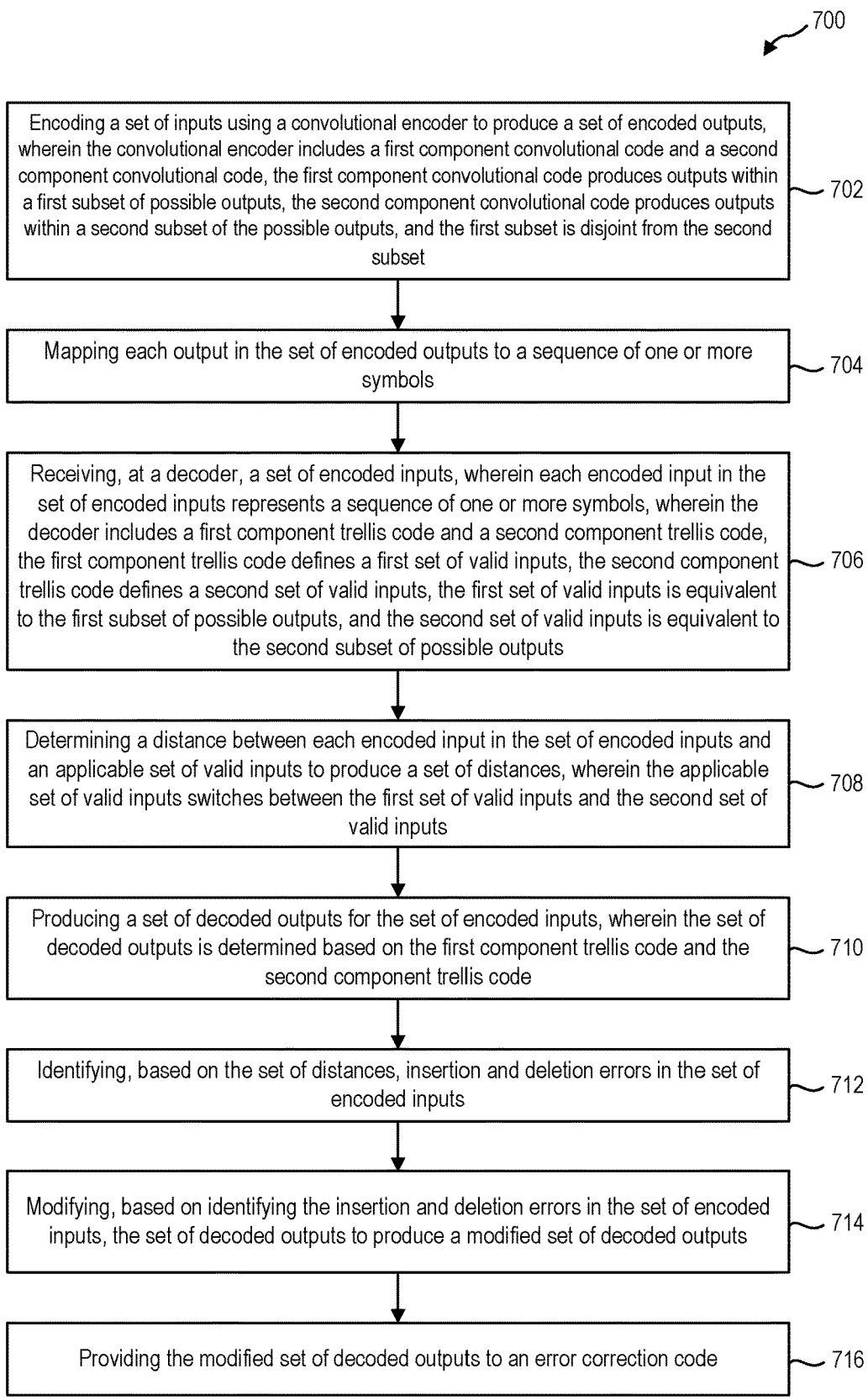
FIG. 7 illustrates an example method for detecting multiple insertion and deletion errors in a signal.

FIG. 7 illustrates an example method 700 for detecting deletion and insertion errors.

The method 700 may include encoding 702 a set of inputs using a convolutional encoder to produce a set of encoded outputs, wherein the convolutional encoder includes a first component convolutional code and a second component convolutional code, the first component convolutional code produces outputs within a first subset of possible outputs, the second component convolutional code produces outputs within a second subset of the possible outputs, and the first subset is disjoint from the second subset. The first component convolutional code and the second component convolutional code may be time interlaced. The convolutional encoder may switch between applying the first component convolutional code and the second component convolutional code. The first component convolutional code and the second component convolutional code may share a set of convolutional memories. The convolutional encoder may determine the set of encoded outputs based on the set of inputs, the set of convolutional memories, and the currently active component convolutional code (either the first component convolutional code or the second component convolutional code).

The method 700 may include mapping 704 each output in the set of encoded outputs to a sequence of one or more symbols. The one or more symbols may be DNA bases.

The method 700 may include receiving 706, at a decoder, a set of encoded inputs, wherein each encoded input in the set of encoded inputs represents a sequence of one or more symbols, wherein the decoder includes a first component trellis code and a second component trellis code, the first component trellis code defines a first set of valid inputs, the second component trellis code defines a second set of valid inputs, the first set of valid inputs is equivalent to the first subset of possible outputs, and the second set of valid inputs is equivalent to the second subset of possible outputs. The set of encoded inputs may be based on the sequence of one or more symbols.

The method may include determining 708 a distance between each encoded input in the set of encoded inputs and an applicable set of valid inputs to produce a set of distances, wherein the applicable set of valid inputs switches between the first set of valid inputs and the second set of valid inputs.

The method may include producing 710 a set of decoded outputs for the set of encoded inputs, wherein the set of decoded outputs is determined based on the first component trellis code and the second component trellis code.

The method may include identifying 712, based on the set of distances, insertion and deletion errors in the set of encoded inputs. Identifying 712 the insertion and deletion errors may include identifying locations of the insertion and deletion errors within the set of encoded inputs.

The method may include modifying 714, based on identifying the insertion and deletion errors in the set of encoded inputs, the set of decoded outputs to produce a modified set of decoded outputs. Modifying 714 the set of decoded outputs to produce the modified set of decoded outputs may be further based on the identified locations of the insertion and deletion errors within the set of encoded inputs.

The method may include providing 716 the modified set of decoded outputs to an error correction code. The error correction code may correct substitution errors in the modified set of decoded outputs.

Figure 8A:
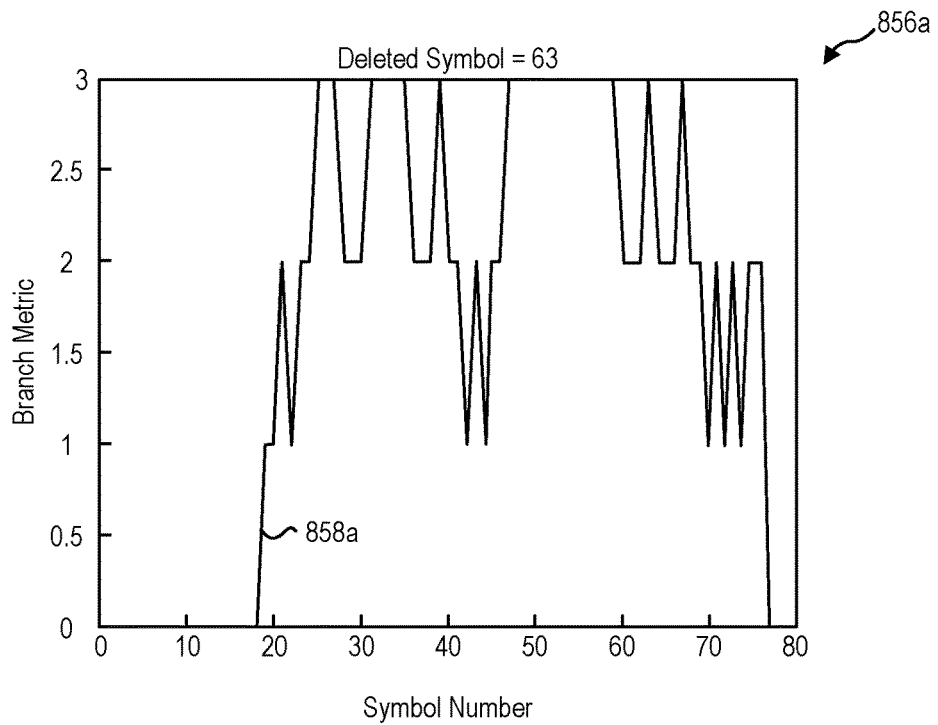
FIGS. 8A-8C illustrate example plots of branch metrics determined by a decoder.
Figure 8A:
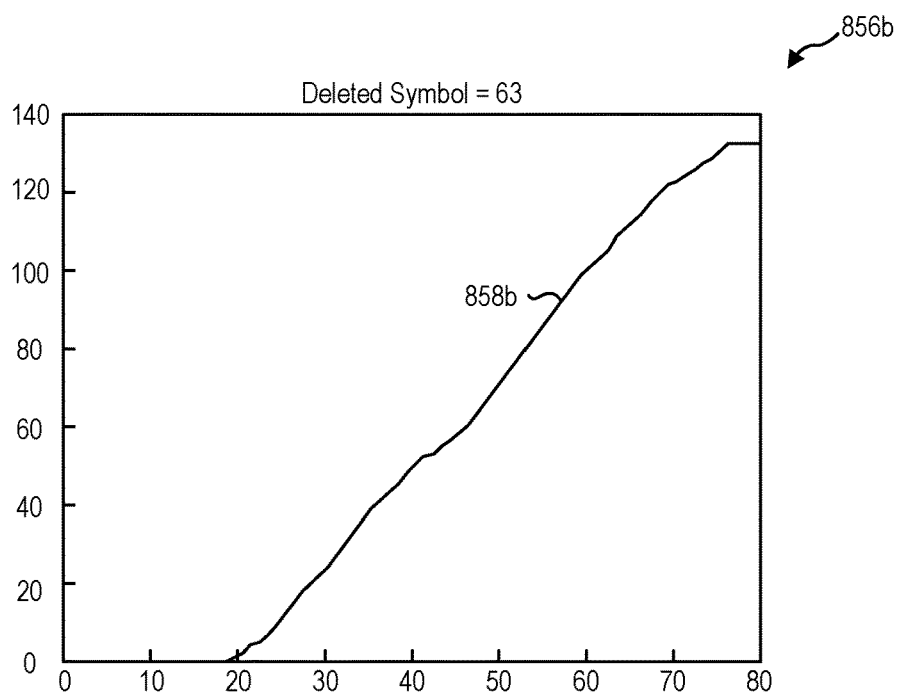

FIG. 8A shows two example graphs, graph 856a and graph 856b. The graph 856a shows plot 858a. The plot 858a shows a branch (distance) metric calculated in a Viterbi algorithm decoder where one symbol has been deleted in a set of encoded inputs. For purposes of this example graph, an encoder used in connection with the decoder may have a code rate of 5/6, receive 400 bits of inputs, and produce 480 bits of outputs. The 480 bits of outputs may be equivalent to 240 DNA bases. The symbol numbers shown on the bottom of the graph 856a may be groupings of three symbols. The deleted symbol may be symbol 63 in the 240 DNA bases. The plot 858a shows that after the symbol is deleted, the branch metrics from that point on are mostly non-zero. There may be a delay in making a decision on each symbol. Meaning, a first output of a decoder may not come immediately after a first input. The decoder may wait to receive a few symbols to compute a distance between a valid path and a received sequence and then make a decision for an earlier symbol. The plot 858b shows the aggregate branch metric.

Figure 8B:
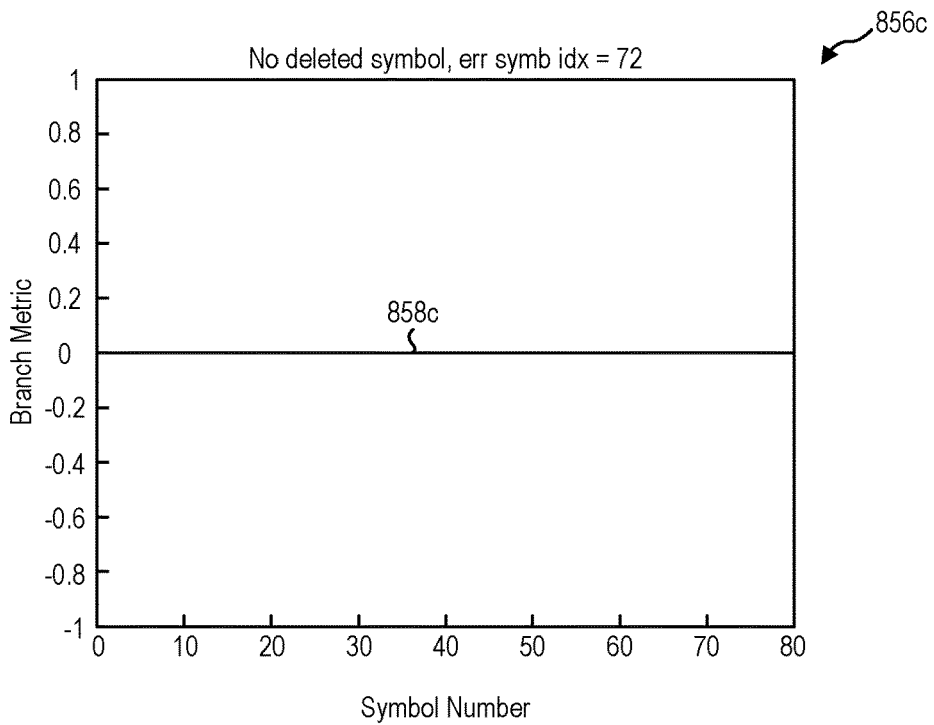
Figure 8B:
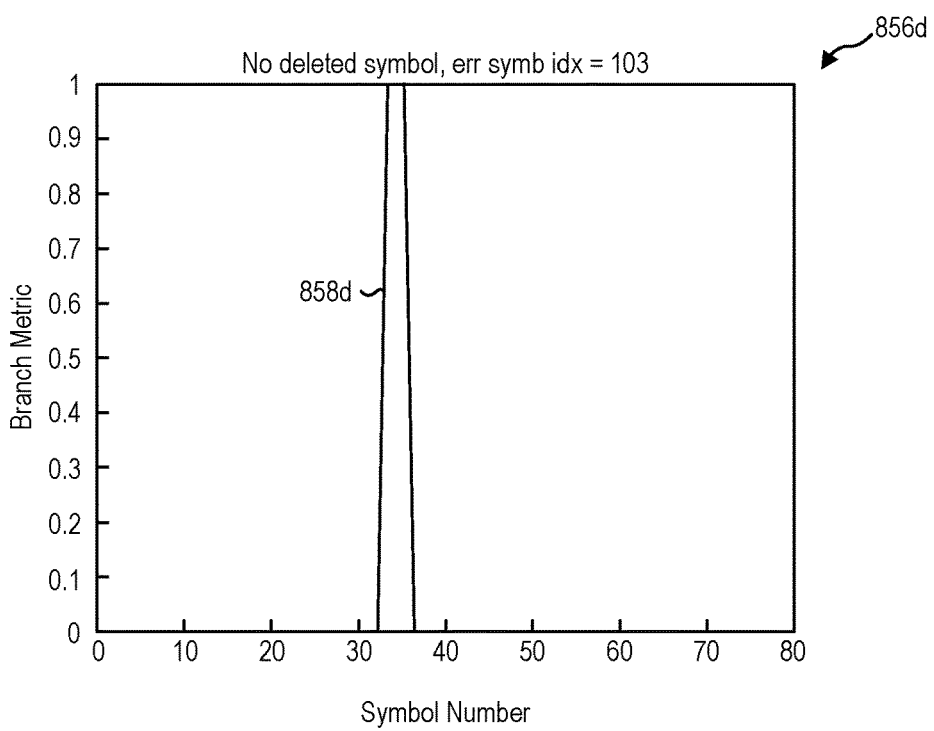

FIG. 8B shows two example graphs, graph 856c and graph 856d. The graph 856c shows plot 858c. The plot 858c shows an example of a case of a substitution error within a corresponding code alphabet. For purposes of this example, it is assumed a decoder was designed such that the decoder may not see the substitution error. In alternative designs, a decoder may detect the substitution error. The graph 856d shows plot 858d. The plot 858d shows a case of a substitution error outside a corresponding code alphabet. The branch metric increases temporarily but settles to zero quickly. This behavior is different from a situation in which there is a deletion error.

The convolutional code can be designed to use maximum protection and sensitivity against deletions and insertions. The convolutional code may be transparent to many errors so that even in presence of multiple errors, the metric behavior is different from that of deletions.

Figure 8C:
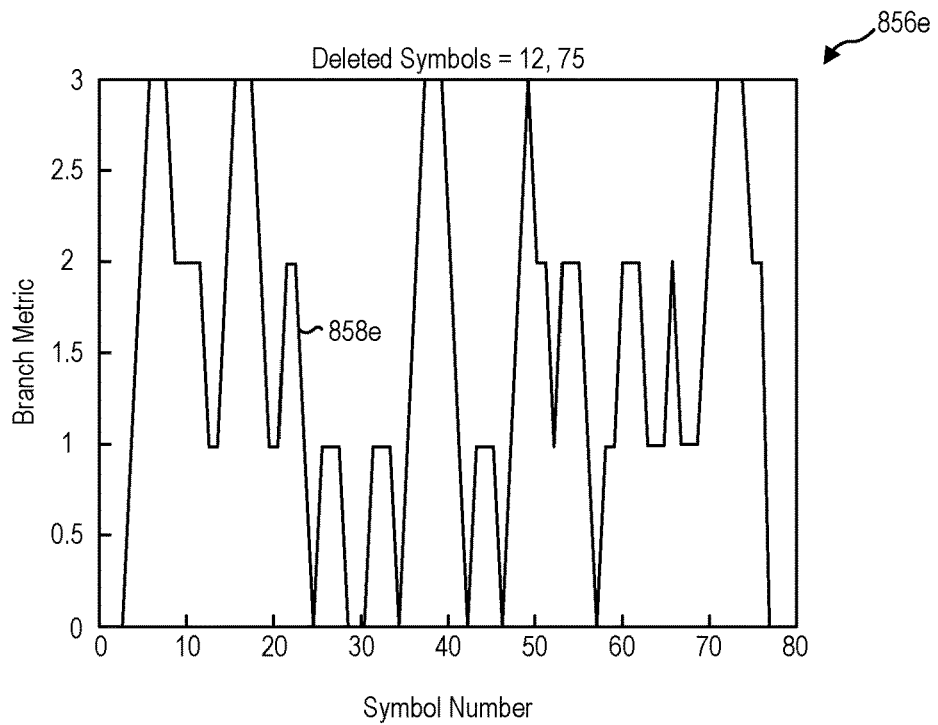
Figure 8C:
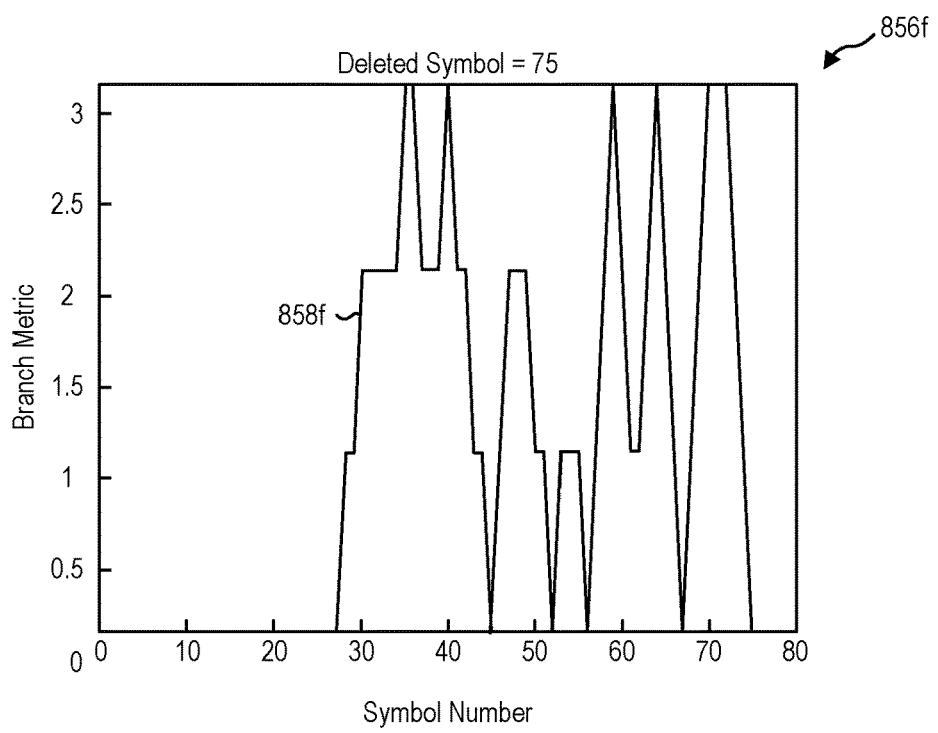

FIG. 8C shows graph 856e and graph 856f. The graph 856e shows plot 858e. The plot 858e shows a case in which two symbols are deleted. In the case of multiple deletions, a decoder may use an iterative process. Suppose symbols 12 and 75 are deleted. Based on branch metrics, the decoder can detect a location of a first deletion as Viterbi algorithm progresses. Based on a first deletion index, a dummy symbol from corresponding code can be added to the sequence and decoding can be repeated to detect the next deletion index. The graph 856f shows plot 858f after the dummy symbol from the corresponding code has been added.

Figure 9:
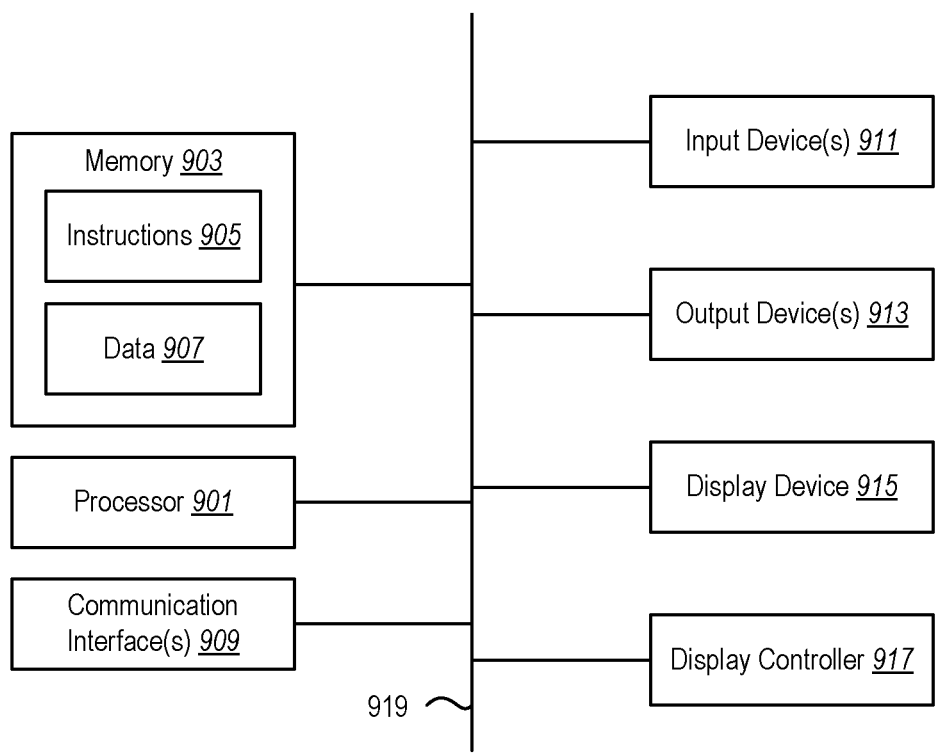
FIG. 9 illustrates example components of a computing device.

Reference is now made to FIG. 9. One or more computing devices 900 can be used to implement at least some aspects of the techniques disclosed herein. FIG. 9 illustrates certain components that can be included within a computing device 900.

The computing device 900 includes a processor 901 and memory 903 in electronic communication with the processor 901. Instructions 905 and data 907 can be stored in the memory 903. The instructions 905 can be executable by the processor 901 to implement some or all of the methods, steps, operations, actions, or other functionality that is disclosed herein. Executing the instructions 905 can involve the use of the data 907 that is stored in the memory 903. Unless otherwise specified, any of the various examples of modules and components described herein can be implemented, partially or wholly, as instructions 905 stored in memory 903 and executed by the processor 901. Any of the various examples of data described herein can be among the data 907 that is stored in memory 903 and used during execution of the instructions 905 by the processor 901.

Although just a single processor 901 is shown in the computing device 900 of FIG. 9, in an alternative configuration, a combination of processors (e.g., an Advanced RISC (Reduced Instruction Set Computer) Machine (ARM) and a digital signal processor (DSP)) could be used.

The computing device 900 can also include one or more communication interfaces 909 for communicating with other electronic devices. The communication interface(s) 909 can be based on wired communication technology, wireless communication technology, or both. Some examples of communication interfaces 909 include a Universal Serial Bus (USB), an Ethernet adapter, a wireless adapter that operates in accordance with an Institute of Electrical and Electronics Engineers (IEEE) 802.11 wireless communication protocol, a Bluetooth® wireless communication adapter, and an infrared (IR) communication port.

The computing device 900 can also include one or more input devices 911 and one or more output devices 913. Some examples of input devices 911 include a keyboard, mouse, microphone, remote control device, button, joystick, trackball, touchpad, and lightpen. One specific type of output device 913 that is typically included in a computing device 900 is a display device 915. Display devices 915 used with embodiments disclosed herein can utilize any suitable image projection technology, such as liquid crystal display (LCD), light-emitting diode (LED), gas plasma, electroluminescence, wearable display, or the like. A display controller 917 can also be provided, for converting data 907 stored in the memory 903 into text, graphics, and/or moving images (as appropriate) shown on the display device 915. The computing device 900 can also include other types of output devices 913, such as a speaker, a printer, etc.

The various components of the computing device 900 can be coupled together by one or more buses, which can include a power bus, a control signal bus, a status signal bus, a data bus, etc. For the sake of clarity, the various buses are illustrated in FIG. 9 as a bus system 919.

The techniques disclosed herein can be implemented in hardware, software, firmware, or any combination thereof, unless specifically described as being implemented in a specific manner. Any features described as modules, components, or the like can also be implemented together in an integrated logic device or separately as discrete but interoperable logic devices. If implemented in software, the techniques can be realized at least in part by a non-transitory computer-readable medium having computer-executable instructions stored thereon that, when executed by at least one processor, perform some or all of the steps, operations, actions, or other functionality disclosed herein. The instructions can be organized into routines, programs, objects, components, data structures, etc., which can perform particular tasks and/or implement particular data types, and which can be combined or distributed as desired in various embodiments.

The term "processor" can refer to a general purpose single- or multi-chip microprocessor (e.g., an Advanced RISC (Reduced Instruction Set Computer) Machine (ARM)), a special purpose microprocessor (e.g., a digital signal processor (DSP)), a microcontroller, a programmable gate array, or the like. A processor can be a central processing unit (CPU). In some embodiments, a combination of processors (e.g., an ARM and DSP) could be used to implement some or all of the techniques disclosed herein.

The term "memory" can refer to any electronic component capable of storing electronic information. For example, memory may be embodied as random access memory (RAM), read-only memory (ROM), magnetic disk storage media, optical storage media, flash memory devices in RAM, various types of storage class memory, on-board memory included with a processor, erasable programmable read-only memory (EPROM), electrically erasable programmable read-only memory (EEPROM) memory, registers, and so forth, including combinations thereof.

The steps, operations, and/or actions of the methods described herein may be interchanged with one another without departing from the scope of the claims. In other words, unless a specific order of steps, operations, and/or actions is required for proper functioning of the method that is being described, the order and/or use of specific steps, operations, and/or actions may be modified without departing from the scope of the claims.

The term "determining" (and grammatical variants thereof) can encompass a wide variety of actions. For example, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The terms "comprising," "including," and "having" are intended to be inclusive and mean that there can be additional elements other than the listed elements. Additionally, it should be understood that references to "one embodiment" or "an embodiment" of the present disclosure are not intended to be interpreted as excluding the existence of additional embodiments that also incorporate the recited features. For example, any element or feature described in relation to an embodiment herein may be combinable with any element or feature of any other embodiment described herein, where compatible.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A non-transitory computer-readable medium comprising instructions that are executable by one or more processors to cause a computing system to:
  receive a first input at a first time;
  determine, using a first set of convolutional code connections, a first output based on the first input and a first state, wherein the first state is contained in convolutional code memories;
  modify the convolutional code memories to generate a second state based on the first state, the first input, and the first set of convolutional code connections;
  receive a second input at a second time after the first time;
  determine, using a second set of convolutional code connections, a second output based on the second input and the second state, wherein the first set of convolutional code connections is configured to produce outputs in a first subset of a set of possible outputs, the second set of convolutional code connections is configured to produce outputs in a second subset of the set of possible outputs, and the first subset is disjoint from the second subset; and modify the convolutional code memories to generate a third state based on the second state, the second input, and the second set of convolutional code connections.

2. The non-transitory computer-readable medium of claim 1, further comprising instructions that are executable by the one or more processors to cause the computing system to:
receive a third input at a third time after the second time;
determine, using the first set of convolutional code connections, a third output based on the third input and the third state; and
modify the convolutional code memories to generate a fourth state based on the third state, the third input, and the first set of convolutional code connections.

3. The non-transitory computer-readable medium of claim 1, further comprising instructions that are executable by the one or more processors to cause the computing system to:
receive a third input at a third time after the second time;
determine, using a third set of convolutional code connections, a third output based on the third input and the third state, wherein the third set of convolutional code connections is configured to produce outputs in a third subset of the set of possible outputs and the third subset is disjoint from the second subset and the first subset; and
modify the convolutional code memories to generate a fourth state based on the third state, the third input, and the third set of convolutional code connections.

4. The non-transitory computer-readable medium of claim 1, further comprising instructions that are executable by the one or more processors to cause the computing system to:
map the first output to a first set of symbols; and
map the second output to a second set of symbols.

5. The non-transitory computer-readable medium of claim 4, wherein the first set of symbols and the second set of symbols represent one or more DNA bases.

6. The non-transitory computer-readable medium of claim 5, wherein the first set of symbols comprises a sequence of one or more DNA bases different from the second set of symbols.

7. The non-transitory computer-readable medium of claim 1, wherein the convolutional code memories comprise two or more memories.

8. The non-transitory computer-readable medium of claim 1, wherein the first input comprises two or more bits and the first output comprises more bits than the first input.

9. A non-transitory computer-readable medium comprising instructions that are executable by one or more processors to cause a computing system to:
receive, at a decoder, a first input at a first time, wherein the decoder has a first state at the first time;
calculate a first distance between the first input and a first set of valid inputs, wherein the first set of valid inputs is defined by a first component trellis code;
determine a second state of the decoder based on the first state, the first input, and the first component trellis code;
receive, at the decoder, a second input at a second time after the first time;
calculate a second distance between the second input and a second set of valid inputs, wherein the second set of valid inputs is defined by a second component trellis code and wherein the second set of valid inputs is disjoint from the first set of valid inputs; and determine a third state of the decoder based on the second state, the second input, and the second component trellis code.

10. The non-transitory computer-readable medium of claim 9, wherein the first distance and the second distance are one or more of L1 distances, L2 distances, or any other distance metric.

11. The non-transitory computer-readable medium of claim 9, further comprising instructions that are executable by the one or more processors to cause the computing system to:
determine, based on the first distance and the second distance, a location of an insertion or deletion error.

12. The non-transitory computer-readable medium of claim 9, further comprising instructions that are executable by the one or more processors to cause the computing system to:
receive a third input at a third time after the second time;
calculate a third distance between the third input and the first set of valid inputs; and
determine a fourth state of the decoder based on the third state, the third input, and the first component trellis code.

13. The non-transitory computer-readable medium of claim 9, further comprising instructions that are executable by the one or more processors to cause the computing system to:
receive a third input at a third time after the second time;
calculate a third distance between the third input and a third set of valid inputs, wherein the third set of valid inputs is defined by a third component trellis code and wherein the third set of valid inputs is disjoint from the first set of valid inputs and the third set of valid inputs; and
determine a fourth state of the decoder based on the third state, the third input, and the third component trellis code.

14. The non-transitory computer-readable medium of claim 9, wherein the first input and the second input are sequenced from DNA storage.

15. The non-transitory computer-readable medium of claim 14, wherein the first input and the second input represent one or more DNA bases.

16. A method for detecting deletion and insertion errors, the method comprising:
encoding a set of inputs using a convolutional encoder to produce a set of encoded outputs, wherein the convolutional encoder includes a first component convolutional code and a second component convolutional code, the first component convolutional code produces outputs within a first subset of a set of possible outputs, the second component convolutional code produces outputs within a second subset of the set of possible outputs, and the first subset is disjoint from the second subset;
receiving, at a decoder, a set of encoded inputs, wherein each encoded input in the set of encoded inputs represents a sequence of one or more symbols, wherein the decoder includes a first component trellis code and a second component trellis code, the first component trellis code defines a first set of valid inputs, the second component trellis code defines a second set of valid inputs, the first set of valid inputs is equivalent to the first subset of possible outputs, and the second set of valid inputs is equivalent to the second subset of possible outputs;

determining a distance between each encoded input in the set of encoded inputs and an applicable set of valid inputs to produce a set of distances, wherein the applicable set of valid inputs switches between the first set of valid inputs and the second set of valid inputs;

producing a set of decoded outputs for the set of encoded inputs, wherein the set of decoded outputs is determined based on the first component trellis code and the second component trellis code;

identifying, based on the set of distances, insertion and deletion errors in the set of encoded inputs; and modifying, based on identifying the insertion and deletion errors in the set of encoded inputs, the set of decoded outputs to produce a modified set of decoded outputs.

17. The method of claim 16, further comprising:
providing the modified set of decoded outputs to an error correction code.

18. The method of claim 16, further comprising:
mapping each output in the set of encoded outputs to a combination of one or more symbols.

19. The method of claim 18, wherein the combination of one or more symbols comprises DNA bases.

20. The method of claim 16, wherein the set of encoded inputs includes substitution errors.

* * * * *